US009211100B2

(12) United States Patent
Ma

(10) Patent No.: US 9,211,100 B2
(45) Date of Patent: *Dec. 15, 2015

(54) PORTABLE RADIOGRAPHIC X-RAY PERIPHERAL BONE DENSITY AND IMAGING SYSTEMS AND METHODS

(71) Applicant: George W. Ma, Irvine, CA (US)

(72) Inventor: George W. Ma, Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/703,110

(22) Filed: May 4, 2015

(65) Prior Publication Data

US 2015/0230765 A1     Aug. 20, 2015

Related U.S. Application Data

(63) Continuation of application No. 13/917,945, filed on Jun. 14, 2013, now Pat. No. 9,044,186.

(60) Provisional application No. 61/664,066, filed on Jun. 25, 2012.

(51) Int. Cl.
*G01B 15/02*     (2006.01)
*A61B 6/00*      (2006.01)

(52) U.S. Cl.
CPC ............. *A61B 6/4042* (2013.01); *A61B 6/461* (2013.01); *A61B 6/467* (2013.01); *A61B 6/482* (2013.01); *A61B 6/505* (2013.01); *A61B 6/563* (2013.01)

(58) Field of Classification Search
CPC ....... A61B 6/4035; A61B 6/505; G01B 5/025
USPC ..................................... 378/51, 54, 156–160
See application file for complete search history.

(56) References Cited

U.S. PATENT DOCUMENTS

| 4,029,963 | A | 6/1977 | Alvarez et al. |
| 4,247,774 | A | 1/1981 | Brooks |
| 4,355,331 | A | 10/1982 | Georges et al. |
| 4,361,901 | A | 11/1982 | Daniels et al. |
| 4,507,799 | A | 3/1985 | Shimkus |
| 4,542,459 | A | 9/1985 | Riederer |
| 4,626,688 | A | 12/1986 | Barnes |
| 4,829,549 | A | 5/1989 | Vogel et al. |

(Continued)

FOREIGN PATENT DOCUMENTS

| CN | 102894988 | 1/2013 |
| EP | 2302644 | 4/2012 |

(Continued)

OTHER PUBLICATIONS

Notice of First Review of Chinese Patent Application 201310397149.3 by Chinese State Intellectual Property Office (SIPO) dated Nov. 17, 2014. (11 pages, no English translation available).

(Continued)

*Primary Examiner* — Courtney Thomas
(74) *Attorney, Agent, or Firm* — Knobbe, Martens, Olson & Bear, LLP

(57) ABSTRACT

Devices, tools, systems and methods for X-ray bone density measurement and imaging for radiography, fluoroscopy and related procedures. Portable, efficient peripheral bone density measurement and/or high resolution imaging and/or small field digital radiography of bone and other tissue, including tissue in the peripheral skeletal system, such as the arm, forearm, leg, hand and/or foot.

19 Claims, 17 Drawing Sheets

(56) References Cited

U.S. PATENT DOCUMENTS

| | | |
|---|---|---|
| 4,947,414 A | 8/1990 | Stein |
| 5,077,771 A | 12/1991 | Skillicorn et al. |
| 5,132,995 A | 7/1992 | Stein |
| 5,138,167 A | 8/1992 | Barnes |
| 5,148,455 A | 9/1992 | Stein |
| 5,150,394 A | 9/1992 | Karellas |
| 5,216,252 A | 6/1993 | Boone et al. |
| 5,247,559 A | 9/1993 | Ohtsuchi et al. |
| 5,253,282 A | 10/1993 | Pelc |
| RE34,511 E | 1/1994 | O'Neill et al. |
| 5,287,546 A | 2/1994 | Tesic et al. |
| 5,291,537 A | 3/1994 | Mazess |
| 5,432,834 A | 7/1995 | Gershman |
| 5,451,793 A | 9/1995 | Boone |
| 5,456,284 A | 10/1995 | Ryan et al. |
| 5,465,284 A | 11/1995 | Karellas |
| 5,657,369 A | 8/1997 | Stein et al. |
| 5,748,704 A | 5/1998 | Mazess et al. |
| 5,838,765 A | 11/1998 | Gershman et al. |
| 5,841,832 A | 11/1998 | Mazess et al. |
| 5,852,647 A | 12/1998 | Schick et al. |
| 5,898,753 A | 4/1999 | Schick et al. |
| 5,910,972 A | 6/1999 | Ohkubo et al. |
| 5,917,877 A | 6/1999 | Chiabrera et al. |
| 5,949,846 A | 9/1999 | Stein et al. |
| 6,058,157 A | 5/2000 | Christiansen et al. |
| 6,086,538 A | 7/2000 | Jorgensen et al. |
| 6,246,745 B1 | 6/2001 | Bi et al. |
| 6,282,258 B1 | 8/2001 | Stein et al. |
| 6,315,445 B1 | 11/2001 | Mazess et al. |
| 6,320,931 B1 | 11/2001 | Arnold |
| 6,393,097 B1 | 5/2002 | Aufrichtig et al. |
| 6,438,201 B1 | 8/2002 | Mazess et al. |
| 6,490,339 B2 | 12/2002 | Mitchell et al. |
| 6,510,197 B1 | 1/2003 | Mitchell et al. |
| 6,574,302 B2 | 6/2003 | Adriaansz |
| 6,597,759 B2 | 7/2003 | Mazess et al. |
| 6,661,873 B2 | 12/2003 | Jabri et al. |
| 6,676,291 B2 | 1/2004 | Ahn |
| 6,683,934 B1 | 1/2004 | Zhao et al. |
| 6,754,306 B2 | 6/2004 | Cho et al. |
| 6,807,249 B2 | 10/2004 | Dinten et al. |
| 6,853,741 B1 | 2/2005 | Ruth et al. |
| 6,873,680 B2 | 3/2005 | Jones |
| 6,909,771 B2 | 6/2005 | Waggener et al. |
| 7,010,092 B2 | 3/2006 | Winsor |
| 7,069,066 B2 | 6/2006 | Zeller et al. |
| 7,174,000 B2 | 2/2007 | Fehre et al. |
| 7,224,769 B2 | 5/2007 | Turner |
| 7,295,691 B2 | 11/2007 | Uppaluri et al. |
| 7,330,531 B1 | 2/2008 | Karellas |
| 7,330,532 B2 | 2/2008 | Winsor |
| 7,336,763 B2 | 2/2008 | Spartiotis et al. |
| 7,388,208 B2 | 6/2008 | Deych |
| 7,415,146 B2 | 8/2008 | Unger et al. |
| 7,489,762 B2 | 2/2009 | Bernhardt |
| 7,499,524 B2 | 3/2009 | Anderton et al. |
| 7,563,026 B2 | 7/2009 | Mandelkern et al. |
| 7,684,544 B2 | 3/2010 | Wilson |
| 7,742,568 B2 | 6/2010 | Smith |
| 7,755,059 B2 | 7/2010 | Liu et al. |
| 7,787,014 B2 | 8/2010 | Serceki |
| 7,796,795 B2 | 9/2010 | Uppaluri et al. |
| 7,957,506 B2 | 6/2011 | Smith |
| 7,997,798 B2 | 8/2011 | Liu et al. |
| 8,031,836 B2 | 10/2011 | Lang et al. |
| 8,031,838 B2 | 10/2011 | Bowers et al. |
| 8,041,008 B2 | 10/2011 | Bowers et al. |
| 8,085,898 B2 | 12/2011 | Agrawal et al. |
| 2001/0048732 A1 | 12/2001 | Wilson et al. |
| 2003/0026385 A1 | 2/2003 | Dinten et al. |
| 2003/0068014 A1 | 4/2003 | Ahn |
| 2004/0190679 A1 | 9/2004 | Waggener et al. |
| 2005/0053199 A1 | 3/2005 | Miles |
| 2007/0140424 A1 | 6/2007 | Sereeki |
| 2007/0143147 A1 | 6/2007 | Petrick et al. |
| 2007/0269010 A1 | 11/2007 | Turner |
| 2010/0111395 A1 | 5/2010 | Tamakoshi |
| 2010/0189224 A1 | 7/2010 | Bowers et al. |
| 2010/0197639 A1 | 8/2010 | Lang et al. |
| 2011/0058726 A1 | 3/2011 | Markwardt et al. |
| 2011/0150175 A1 | 6/2011 | Hsieh et al. |
| 2011/0317813 A1 | 12/2011 | Matsushita et al. |
| 2012/0027283 A1 | 2/2012 | Lang et al. |
| 2013/0343519 A1* | 12/2013 | Ma .................................. 378/54 |

FOREIGN PATENT DOCUMENTS

| | | |
|---|---|---|
| JP | 2006-271437 | 10/2006 |
| JP | 2011-244889 | 12/2011 |

OTHER PUBLICATIONS

Notice of Second Review of Chinese Patent Application 201310397149.3 by Chinese State Intellectual Property Office (SIPO) dated Jun. 3, 2015. (13 pages, no English translation available).

\* cited by examiner (Single energy radiography, single exposure)

(Single energy radiography, continued pulse exposure)

Density Imaging

Radiographic Imaging

PORTABLE RADIOGRAPHIC X-RAY PERIPHERAL BONE DENSITY AND IMAGING SYSTEMS AND METHODS

CROSS-REFERENCE TO RELATED APPLICATIONS

This application claims the benefit of priority to U.S. application Ser. No. 13/917,945, filed on Jun. 14, 2013 which claims benefit of provisional Application No. 61/664,066, filed on Jun. 25, 2012, which is incorporated in its entirety by reference herein. Any and all priority claims identified in the Application Data Sheet, or any correction thereto, are hereby incorporated by reference under 37 CFR 1.57.

BACKGROUND

1. Field

Embodiments of the present invention generally relate to devices, tools, systems and methods for X-ray bone density measurement and imaging for radiography, fluoroscopy and related procedures. More specifically, embodiments of the present invention relate to devices, tools, systems and methods for portable, efficient peripheral bone density measurement and/or high resolution imaging and/or small field digital radiography and/or fluoroscopy of bone and other tissue, including tissue in the peripheral skeletal system, such as arms, legs, hands and feet. In one embodiment, a system uses single energy. In one embodiment, a system uses dual energy.

2. Description of the Related Art

Osteoporosis is a systemic skeletal disease characterized by low bone density and microarchitectural deterioration of bone tissue with a consequential increase in bone fragility. Osteoporosis affects an estimated 75 million people in Europe, the United States and Japan. The estimated cost of osteoporotic fracture care exceeds $13-18 billion annually in the United States alone. Diagnosis of osteoporosis is currently generally performed by measurement of bass mass loss or Bone Mineral Density ("BMD").

Presently, three major types of bone densitometers are commercially available: Dual-Energy X-ray Absorptiometry ("DXA"), Quantitative Ultrasound ("QUS") and Quantitative Computed Tomography ("QCT"). DXA is often regarded as a gold standard for BMD and bone loss assessment, due in part to its high precision and low radiation dose. However, the current standard tests performed by whole-body DXA scanner systems are expensive with limited availability in large hospitals and medical imaging centers in cities. Further, most DXA systems are very large to account for the power requirements in conducting full body scanning. Many commonly used bone densitometers in the United States, Europe and Canada are whole-body DXA scanners. In general, current conventional DXA technology uses a fan beam geometry with imaging quality that is relatively poor. There is need for low-cost, portable, wireless capable diagnostic imaging devices that can be used at the point-of-patient care for disadvantaged and under-served populations, including those in remote or rural communities and small hospitals throughout the world.

SUMMARY

Further areas of applicability will become apparent from the description provided herein. It should be understood that the description and specific examples are intended for purposes of illustration only and are not intended to limit the scope of the embodiments disclosed herein.

In one embodiment, a portable, dual-energy radiographic x-ray imaging and bone density measuring system includes an X-ray tube, an X-ray imaging detector, a housing, and an embedded system. The X-ray tube is configured to emit an X-ray beam through a filter positioning mechanism. The filter positioning mechanism includes a high energy filter, a low energy filter, and a shutter configured to block transmission of the X-ray beam. The housing positions the X-ray tube at a distance from the X-ray beam detector, wherein the housing is configured for positioning a forearm between the X-ray tube and the X-ray beam detector. The embedded system is configured to activate the X-ray tube and to control the position of the filter positioning mechanism and imaging data acquisition. In one embodiment, the embedded system is an operating system. In one embodiment, the embedded system manages power requirements, processes data, controls LCD/touchscreen and all system communications that includes USB and wireless communications.

In one embodiment, the X-ray tube is active for at most two seconds per exposure. In one embodiment, the high energy filter provides a high energy component for transmission through the filter positioning mechanism, and limits low energy transmission. In one embodiment, the high energy filter absorbs lower energy. In one embodiment, the high energy filter provides a high energy component of 40-50 kV or more for transmission through the filter positioning mechanism. In one embodiment, the high energy filter comprises copper and at least one of the group consisting of tin and rhodium. In one embodiment, the low energy filter provides for lower energy transmission of energy through the filter positioning mechanism. In one embodiment, the low energy filter provides for lower energy transmission of energy below 40-50 kV through the filter positioning mechanism. In one embodiment, the low energy filter comprises aluminum and at least one type of material having a K-edge absorption of 40 kV or more. In one embodiment, a material having a K-edge absorption of 40 kV or more is selected from the group consisting of cerium, samarium, gadolinium, and barium.

In one embodiment, the filter positioning mechanism is actuated by a stepper motor in electric communication with the embedded system. In one embodiment, the filter positioning mechanism is a filter exchanger configured to be rotatably or linearly actuated by a stepper motor. In one embodiment, the stepper motor is a high torque and high speed design that enables to switch one position to another in 100 ms or less. In one embodiment, the embedded system provides high-speed/high bandwidth data transmission configured for transmission of imaging data in less than 100 ms. In one embodiment, the X-ray imaging detector transmits image data through any one of the group consisting of a Gig-Ethernet and a camera link. In one embodiment, the embedded chip system operates the X-ray tube at a duty cycle of approximately 1/60, for a one second active pulsed radiation to sixty second inactive period. In one embodiment, the embedded chip system operates the X-ray tube at a duty cycle for a two second active pulsed radiation to one hundred twenty second inactive period. In one embodiment, the embedded can include an operating system configured to process data, control a LCD/touchscreen, manage a power supply, and/or control a communication with any of a wired communication, a USB communication and/or a wireless communication. In one embodiment, the system is configured as a battery powered device.

In one embodiment, a method for measuring peripheral bone density includes positioning a forearm of a patient between an X-ray source and a beam detector in an X-ray system. The X-ray tube is configured to emit an X-ray beam through a filter positioning mechanism. The filter positioning mechanism includes a high energy filter, a low energy filter, and a shutter configured to block transmission of the X-ray beam. The method includes activating an embedded chip in the X-ray system, with the embedded chip configured to activate the X-ray tube and to control the position of the filter positioning mechanism. In one embodiment, the activating the embedded chip includes activating the X-ray tube for two seconds or less, moving the filter positioning mechanism from a shuttered position to a low energy position with said high energy filter, acquiring low energy data, moving the filter positioning mechanism from the low energy position to a high energy position with said low energy filter, and acquiring high energy data.

In one embodiment, a method for measuring peripheral bone density includes positioning a forearm of a patient between an X-ray source and a beam detector in an X-ray system. The X-ray tube is configured to emit an X-ray beam through a filter positioning mechanism, the filter positioning mechanism comprising a first energy filter, a second energy filter, and a shutter configured to block transmission of the X-ray beam. In one embodiment, a step includes activating an embedded chip in said X-ray system, the embedded chip configured to activate the X-ray tube and to control the position of the filter positioning mechanism. In one embodiment, a step includes activating the X-ray tube for two seconds or less. In one embodiment, a step includes moving the filter positioning mechanism from a shuttered position to a first energy position with said first energy filter. In one embodiment, a step includes acquiring first energy data. In one embodiment, a step includes moving the filter positioning mechanism from the first energy position to a second energy position with said second energy filter. In one embodiment, a step includes acquiring second energy data.

In one embodiment, a portable, single-energy radiographic x-ray system includes an X-ray monoblock configured to emit an X-ray beam through a filter positioning mechanism, the filter positioning mechanism including a high energy filter, a low energy filter, and a shutter configured to block transmission of the X-ray beam. In one embodiment, the system includes an X-ray imaging detector. In one embodiment, the system includes an anti-scattering grid between the X-ray monoblock and the X-ray imaging detector. In one embodiment, the system includes a housing positioning the X-ray source at a distance from the X-ray beam detector, wherein the housing is configured for positioning a portion of a body between the X-ray source and the X-ray beam detector. In one embodiment, the system includes an embedded system configured to activate the X-ray source and to control the position of the filter positioning mechanism and imaging data acquisition. In one embodiment, the system is configured for single exposure. In one embodiment, the system is configured for continued pulse exposure. In one embodiment, the system is configured as a battery powered device.

In various embodiments, any combination of features from any embodiments may be substituted, combined, or varied.

BRIEF DESCRIPTION OF THE DRAWINGS

The drawings described herein are for illustration purposes only and are not intended to limit the scope of the present disclosure in any way. Embodiments of the present invention will become more fully understood from the detailed description and the accompanying drawings wherein.

DETAILED DESCRIPTION

Figure 1:
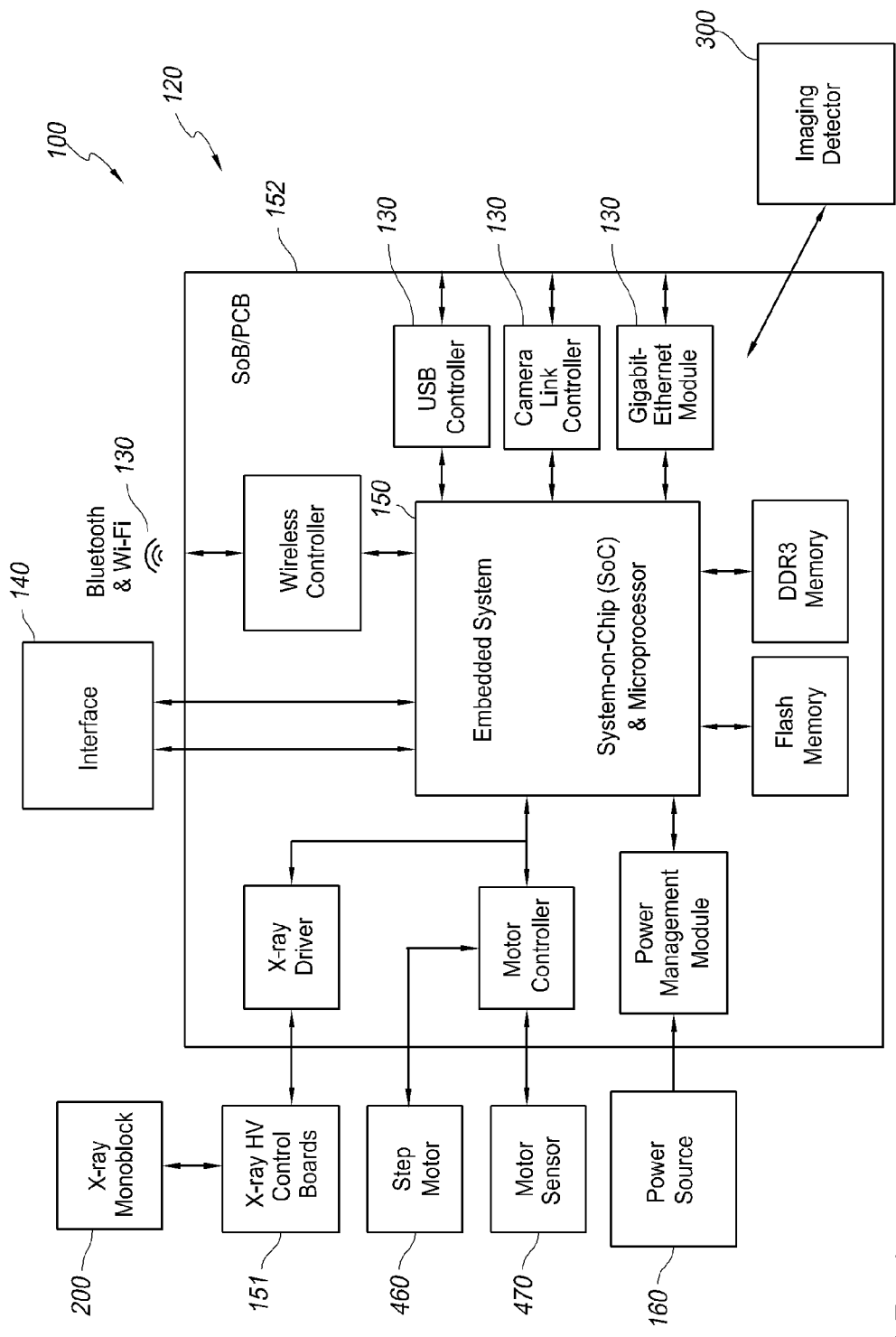
FIG. 1 is a block schematic diagram view of an X-ray system according to an embodiment of the present invention.

The following description sets forth examples of embodiments, and is not intended to limit the present invention or its teachings, applications, or uses thereof. It should be understood that throughout the drawings, corresponding reference numerals indicate like or corresponding parts and features. The description of specific examples indicated in various embodiments of the present invention are intended for purposes of illustration only and are not intended to limit the scope of the invention disclosed herein. Moreover, recitation of multiple embodiments having stated features is not intended to exclude other embodiments having additional features or other embodiments incorporating different combinations of the stated features. Further, features in one embodiment (such as in one figure) may be combined with descriptions (and figures) of other embodiments.

In various embodiments, an X-ray system 100 can be configured for various uses, improvements, and/or advantages over existing systems. For example, conventional technology for assessing fracture risk through measurement of bone density or bone mineral density (BMD) tends to be large, bulky, complex, and/or costly for many people at risk of bone fractures. Other conventional lower cost diagnostic systems may be inaccurate or lack sufficient resolution for diagnosing bone fracture and/or density risk. Difficulty in accessing conventional diagnostic systems may lead to under identification of bone fracture risk, which can cause significant increases in overall healthcare costs.

In various embodiments of the present invention, an X-ray system 100 is configured to assess and/or diagnose bone fracture risk through the assessment of bone mineral density, bone structure, or both. In one embodiment, an X-ray system 100 is configured with enhanced spatial resolution. In one embodiment, an X-ray system 100 is configured with enhanced temporal resolution. In one embodiment, an X-ray system 100 is configured with enhanced specificity. In one embodiment, an X-ray system 100 is configured for BMD measurement. In one embodiment, an X-ray system 100 is configured to perform bone geometric analysis. In one embodiment, an X-ray system 100 is configured to perform bone strength analysis. In various embodiments, any number of X-ray system 100 embodiments can be combined or arranged with any embodiments, components, functions, and/or capabilities.

In one embodiment, an X-ray system 100 is a radiography and/or imaging system. In one embodiment, an X-ray system 100 is a bone density measuring system. In one embodiment, an X-ray system 100 is a radiography imaging system and a bone density measuring system. In one embodiment, an X-ray system 100 is a combination of any of the embodiments or components, functions, and/or capabilities. In one embodiment, an X-ray system 100 is a dual-function system. In one embodiment, an X-ray system 100 is a digital radiography system. In one embodiment, an X-ray system 100 is a dual energy X-ray absorptiometry (DXA) system. In one embodiment, an X-ray system 100 is configured for use on the peripheral skeletal system. In one embodiment, an X-ray system 100 is a mobile forearm digital radiography and dual-energy X-ray absorptiometry system. In one embodiment, an X-ray system 100 is configured as a battery powered device.

In some embodiments, an X-ray system 100 is configured for one or more functions. In one embodiment, an X-ray system 100 is configured for small field radiography. In one embodiment, an X-ray system 100 is configured for imaging and/or bone density measurements of the arm, forearm, hand, finger, wrist, leg, ankle, heal, foot, and/or toe. In one embodiment, an X-ray system 100 is configured for superior imaging for analyzing bone structure/strength (such as bone geometry, cortical bone thickness, etc.). In one embodiment, an X-ray system 100 is configured to use both diagnostic and density images for bone age assessment. In one embodiment, an X-ray system 100 is configured for forearm bone density screening. In one embodiment, an X-ray system 100 is configured for testing of ultra-distal ("UD") radius and/or at the 33% radius for a dominate arm, a non-dominate arm, or both. Because the ultradistal radius region of interest (UDR) has a greater ratio of trabecular to cortical bone than midshaft portions of the radius, it is possible that more patients would be classified as osteoporotic if the UDR is measured. In 2004, the ISCD (Internal Society of Clinic Densitometry) published its official position recommending the 33% radius as a region of interest. In one embodiment, an X-ray system 100 is configured for small animal research. In one embodiment, an X-ray system 100 is configured for laboratory research.

BMD can be measured in terms of T-scores categories from the World Health Organization ("WHO"), which is generally based on bone density in white women. For example, in white adult women, a normal bone T-score is greater than −1. Osteopenia corresponds to a T-score between −1 and −2.5. Osteoporosis has a T-score less than −2.5. Severe (established) osteoporosis T-scores are less than −2.5. In making adjustments to categorizations of BMD measurement in other ethnic groups, men, and children, there are a number of considerations that certain embodiments of the present invention can address.

Generally, comparing the bone mineral density of children to the reference data of adults (to calculate a T-score) will underestimate the BMD of children, because children have less bone mass than fully developed adults. The WHO classification of osteoporosis and osteopenia in adults cannot be applied to children. This would lead to an over-diagnosis of osteopenia for children. To avoid an overestimation of bone mineral deficits, BMD scores are commonly compared to reference data for the same gender, ethnicity and age, such as through Z-score measurements. Also, there are other variables in addition to age that are suggested to confound the interpretation of BMD as measured by DXA. One important confounding variable is bone size. DXA has been shown to overestimate the bone mineral density of taller subjects and underestimate the bone mineral density of smaller subjects. This error is due to the way by which general DXA calculates BMD. In DXA, bone mineral content (measured as the attenuation of the X-ray by the bones being scanned) is divided by the area (also measured by the machine) of the site being scanned. Because general or standard DXA calculates BMD using area (aBMD: areal Bone Mineral Density), it is not an accurate measurement of true bone mineral density, which is mass divided by a volume. In order to distinguish DXA BMD from volumetric bone-mineral density, researchers sometimes refer to DXA BMD as an areal bone mineral density (aBMD). The confounding effect of differences in bone size is due to the missing depth value in the calculation of bone mineral density. Methods to correct for this shortcoming include the calculation of a volume that is approximated from the projected area measure by DXA. DXA BMD results adjusted in this manner are referred to as the bone mineral apparent density (BMAD) and are a ratio of the bone mineral content versus a cuboidal estimation of the volume of bone. Like the results for aBMD, BMAD results do not accurately represent true bone mineral density, since they use approximations of the bone's volume. BMAD is used primarily for research purposes and is not yet used in clinical settings. Some clinics may routinely carry out DXA scans on children with conditions such as nutritional rickets, lupus, and Turner Syndrome. DXA has been demonstrated to measure skeletal maturity and body fat composition and has been used to evaluate the effects of pharmaceutical therapy. It may also aid health professionals in diagnosing and monitoring treatment of disorders of bone mass acquisition in childhood.

In one embodiment, an X-ray system 100 is configured for use with an aging population. In one embodiment, an X-ray system 100 is configured for use in diagnosing osteoporosis. In one embodiment, an X-ray system 100 is configured for use in pediatrics. In one embodiment, an X-ray system 100 is configured for diagnosis or assessment of bone age growth in children. In one embodiment, an X-ray system 100 is configured to identify growth disorders. In one embodiment, an X-ray system 100 is configured for predicting adult height. In one embodiment, an X-ray system 100 is used in conjunction with drug treatment and/or therapy to monitor progress and/or effectiveness of a drug or therapy. In one embodiment, an X-ray system 100 is configured for small field radiography. In one embodiment, an X-ray system 100 is configured for small animal research. In some embodiments, an X-ray system 100 can be a low cost device (for example, in comparison to total body DXA scanner or QCT systems).

Figure 2:
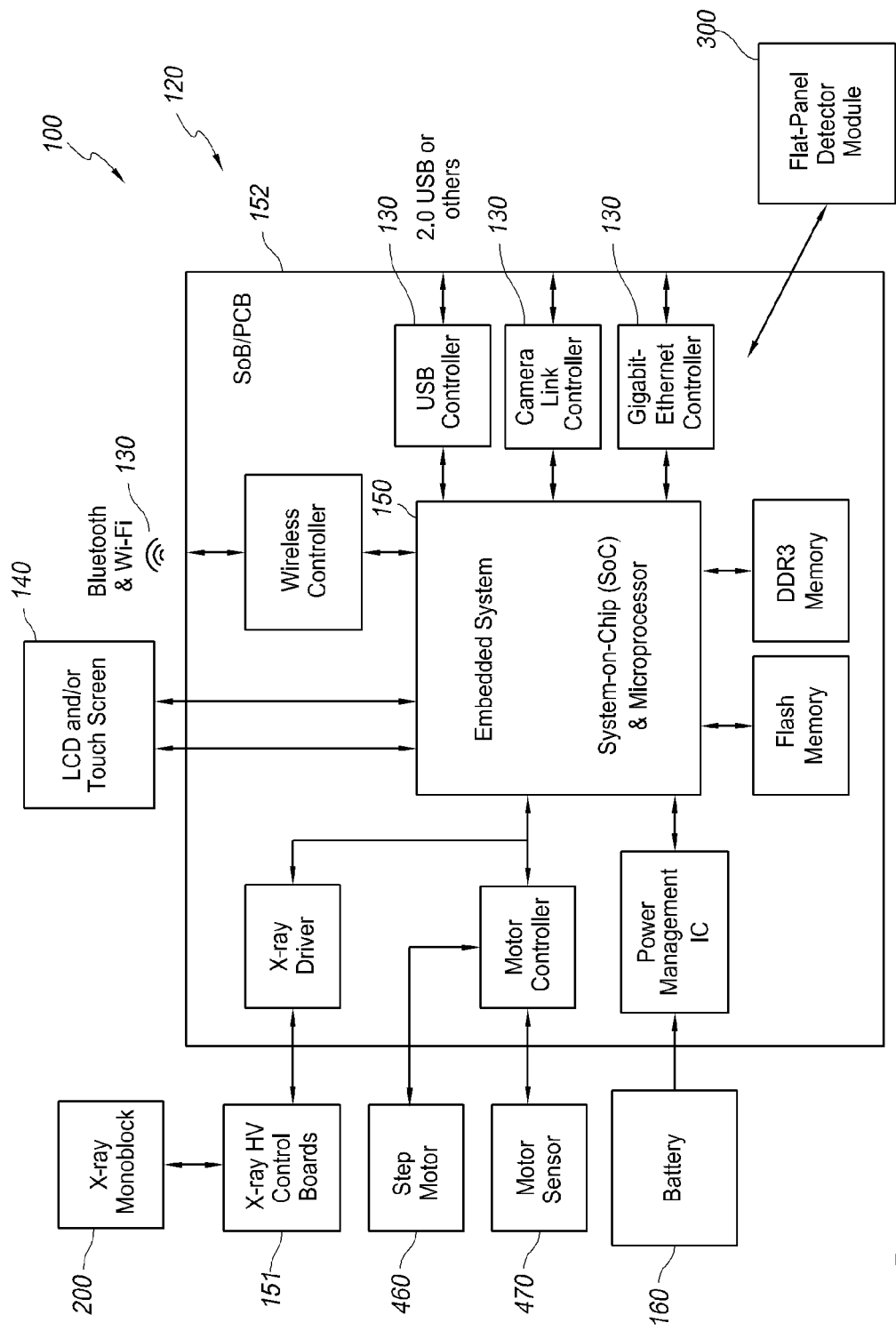
FIG. 2 is a block schematic diagram view of an X-ray system according to an embodiment of the present invention.
Figure 3:
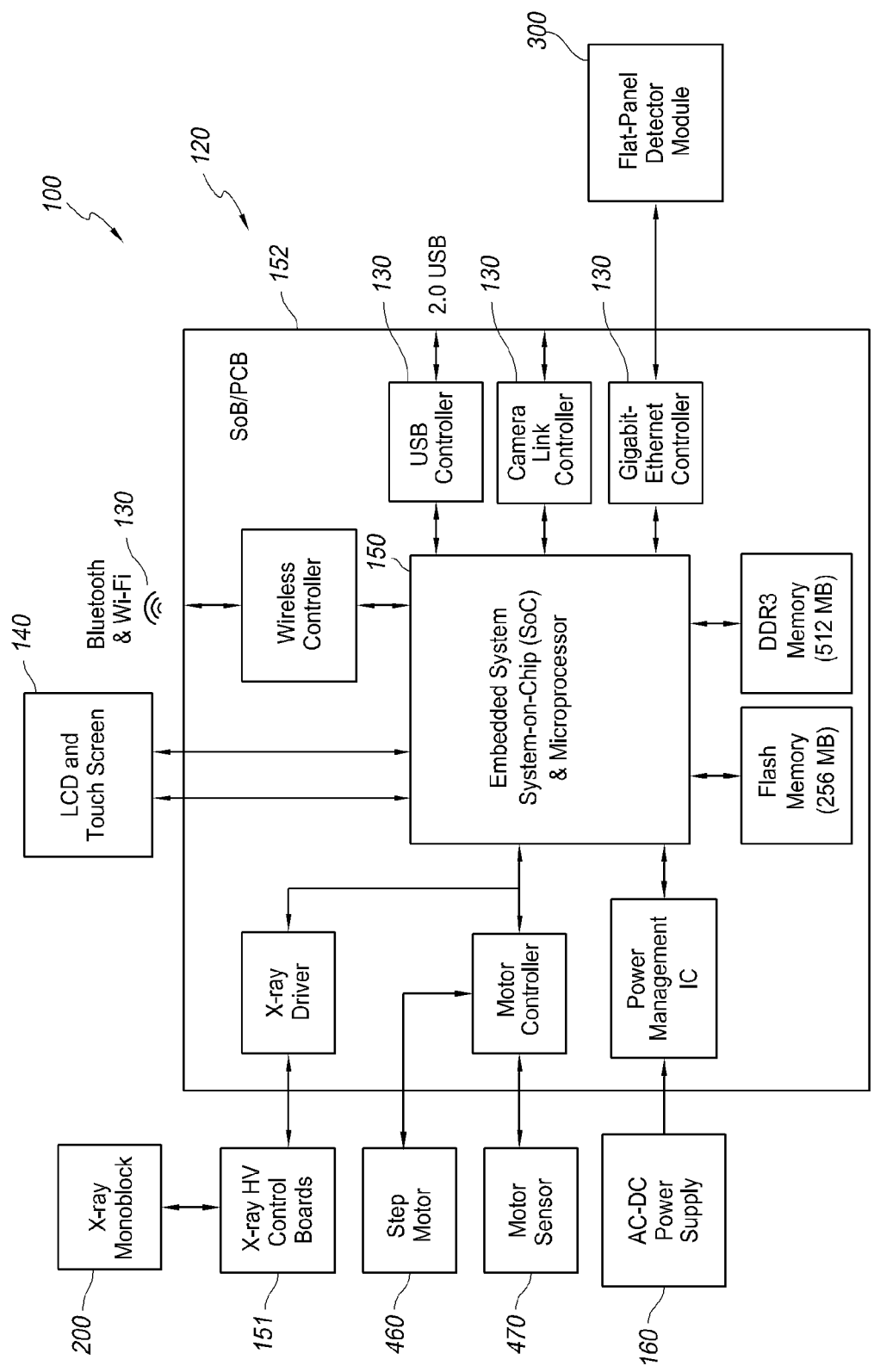
FIG. 3 is a block schematic diagram view of an X-ray system according to an embodiment of the present invention.

FIGS. 1-3 illustrate various schematic embodiments of an X-ray system 100 with various components 110 (not shown in the drawing). Any component 110 can be used in any embodiment with or without any other component 110. In one embodiment, an X-ray system 100 is configured for low cost manufacturing. In one embodiment, an X-ray system 100 is configured for low cost service. In one embodiment, an X-ray system 100 is configured for Design For Manufacturability (DFM) that enhances system integration. In one embodiment, an X-ray system 100 is configured for DFM with any component 110. In various embodiments, various components 110 include any device, module, interface, system, connector, or other unit. In one embodiment, X-ray imaging data is acquired from flat-panel imaging detector through Gig Ethernet. In one embodiment, X-ray imaging data is acquired from flat-panel imaging detector through Camera Link.

In various embodiments, an X-ray system 100 comprises a housing 120. In one embodiment, the housing 120 is an enclosure built to contain other components of the X-ray system 100. In one embodiment, an X-ray system 100 comprises an improved form factor. In one embodiment, an X-ray system 100 is a portable system. In one embodiment, an X-ray system 100 is a mobile system. In one embodiment, a portable X-ray system 100 is configured with a housing 120 for greater mobility based on a relatively small form factor and light weight. In one embodiment, an X-ray system 100 can be hand carried. In some embodiments, an X-ray system 100 can be 40 pounds or lighter. In some embodiments, an X-ray system 100 can be 30 pounds or lighter. In some embodiments, an X-ray system 100 can be 25 pounds or lighter. In some embodiments, an X-ray system 100 can be 20 pounds or lighter. In some embodiments, an X-ray system 100 can be 15 pounds or lighter. In some embodiments, an X-ray system 100 can be 10 pounds or lighter. In some embodiments, an X-ray system 100 can be 5 pounds or lighter. In some embodiments, an X-ray system 100 can have a maximum weight of any weight in the range of 0-50 pounds, 10-40 pounds, 10-30 pounds, 10-20 pounds, 10-15 pounds, 15-20 pounds, or any other amount or range therein. In one embodiment, an X-ray system 100 is between 10-15 pounds. In one embodiment, an X-ray system 100 is between 10-20 pounds. In some embodiments, an X-ray system 100 can be hand carried. In some embodiments, an X-ray system 100 can fit into any room in any setting, such as a clinic, doctor office, medical professional unit, tent, mobile unit, triage center, or other locations. In some embodiments, an X-ray system 100 has various dimensions for improved portability, such as a length, width and/or height of approximately 100 cm, 90 cm, 80 cm, 70 cm, 60 cm, 50 cm, 40 cm, 30 cm, 20 cm, 10 cm or less, or of any range therein. In one embodiment, an X-ray system 100 is configured to have a physical size dimension of approximately 35 cm in length, 35 cm in width, and 50 cm in height. In some embodiments, an X-ray system 100 has various dimensions for improved portability, such as a length, width and/or height of approximately 30, 25, 20, 15, 10, 5 inches or less, or of any range therein. In one embodiment, an X-ray system 100 is configured to have a physical size dimension of approximately 14 by 9 inches for a footprint.

In some embodiments, an X-ray system 100 comprises components 110 that can communicate and/or be attached to one or more other components 110. In one embodiment, components 110 are connected within the housing 120. In one embodiment, components 110 are connected outside the housing 120. In one embodiment, components 110 are connected within and outside the housing 120. In one embodiment, an X-ray system 100 is configured for improved connectivity. In some embodiments, an X-ray system 100 comprises a hard-wired connection to other external electronic equipment. In some embodiments, an X-ray system 100 comprises a wireless connection to other external electronic equipment. In some embodiments, an X-ray system 100 comprises a connector 130. In various embodiments, a connector 130 can be any one (or more) of a USB connection 132, a wireless connection 134, a Blue-tooth/Wi-Fi connection 136, and/or another connection. In some embodiments, an X-ray system 100 is self contained and does not need a connector 130, cable/wire, extra interface or an external computer or personal computer to operate it. In various embodiments, an X-ray system 100 comprises an interface 140. In one embodiment, the interface 140 is one or more keys, buttons, keyboards, switches, or other communication interfaces. In one embodiment, the interface 140 is a touch screen. In one embodiment, the interface 140 is a display. In one embodiment, the interface 140 is a liquid crystal display (LCD). In one embodiment, the interface 140 is LCD touch screen. In various embodiments, the interface 140 can display an image, data, information, and/or status from the X-ray system 100. In various embodiments, the interface 140 can be used to input data, information, instructions, or other in to the X-ray system 100.

In one embodiment, an X-ray system 100 comprises an embedded system 150. In various embodiments, an embedded system can comprise a chip, CPU, and/or a System-on-chip (SoC) that can include a microprocessor, other integrated circuits (ICs), and/or any electronic control system. In one embodiment, an embedded system is an operating system. In one embodiment, an embedded system manages power requirements, processes data, controls LCD/touchscreen and all system communications, including USB and/or wireless communications. In one embodiment, an X-ray system 100 comprises an embedded system 150 powered by a System-on-Chip (SoC). In one embodiment, an X-ray system 100 comprises an embedded system 150 powered by a custom designed printed-circuitry-board (PCB)/System-on-Board (SoB 152). In one embodiment, an X-ray system 100 comprises an embedded system 150 powered by SoC and SoB 152. In one embodiment, an X-ray system 100 comprises an embedded system 150 configured for enhanced system performance, especially for high-speed/high-bandwidth interconnectivity and data management. In one embodiment, an X-Ray control board 151 is used to control an X-Ray tube. In one embodiment, an X-ray system 100 is configured for reduced material cost, resulting in a reduced BOM (Bill of Material) cost. In one embodiment, an X-ray system 100 uses relatively fewer components 110 and materials than other conventional systems. In one embodiment, a SoB 152 can have several chip (or ICs) and special circuit designs in order to control and manage a number of peripheral devices (such as a LCD/touch screen, motor, X-ray power supply, etc.). In one embodiment, a SoB 152 integrates multiple functions into one single piece of board. In various embodiments, X-ray and stepper motor controllers control X-ray and motor actions. In various embodiments, power management module can provide power requirements to any or all peripheral devices. SoB 152 has wire, wireless and display/touchscreen interfaces. In various embodiments, the SoB 152 includes a Gig-Ethernet, a Camera Link, and/or DDR3 memory designs for high-speed/high-bandwidth data transmission and storage.

In one embodiment, an X-ray system 100 obtains power from a power source 160. In various embodiments, the power source is AC, DC, AC/DC, a battery, or other power source. In one embodiment, an X-ray system 100 is configured for AC power. In one embodiment, an X-ray system 100 is configured for DC power. In one embodiment, an X-ray system 100 is configured to be convertible to a battery powered device. In one embodiment, an X-ray system 100 is configured to be a battery powered device.

In one embodiment, an X-ray system 100 comprises an X-ray tube 200. In one embodiment, the X-ray source is an X-ray monoblock containing an X-ray tube and an X-ray HV board 200 potted inside. In various embodiments, any X-ray source can be an X-ray monoblock. X-rays are generally produced when an electron beam is accelerated by high voltage (usually in a range from about 40 to 150 kV) then is suddenly decelerated as it hits a metal target (such as Tungsten, Molybdenum or Rhenium) in a vacuum tube. In one embodiment, the X-ray tube 200 is submerged in high-density insulation oil or some other medium contained in the metal housing. Some metal housings are made of aluminum, steel or lead. This typical reaction results in about 1% of kinetic energy being converted into X-ray radiation, with the remaining roughly 99% of the kinetic energy becoming heat that needs to be dissipated to avoid overheat or damage to the system. In some embodiments, the X-ray tube 200 is cooled. Cooling is generally provided by the insulation oil and can be circulated by pump through air or water or other media for cooling. In one embodiment, the X-ray HV supply is potted inside a monoblock to avoid potential hazards of high voltage exposure to humans and/or the external environment. In general, many medical X-ray devices operate at a continuous duty cycle. As a result, most medical X-ray devices are heavy and too bulky to be portable.

One way to reduce the potential of overheating in generating X-ray radiation is to shorten X-ray radiation exposure by changing the duty cycle 210 to allow self-cooling. Thus, in one embodiment, an X-ray system 100 can operate under a reduced duty cycle 210 instead of continuously generating heat with a continuous duty cycle. In one embodiment, an X-ray system 100 needs less than 1 second for a single exposure. In one embodiment, an X-ray system 100 needs less than 2 seconds for a single exposure. In one embodiment, an X-ray system 100 needs less than 3 seconds for a single exposure. In some embodiments, an X-ray system 100 is configured for a fast examination. This helps eliminate artifacts due patient motion and reduces radiation exposure time. In various embodiments, an X-ray system 100 is configured for a 1 second to 1.5 second total exposure time for dual-energy densitometry and less than 2 second total exam time. In various embodiments, exposure times can be 5, 4.5, 4, 3.5, 3, 2.5, 2, 1.5, 1, and/or 0.5 seconds or less.

In one embodiment, an X-ray system 100 incorporates an imaging detector 300 and a light-weight X-ray tube 200 that is encapsulated in low-density insulating materials, such as silicon rubber, to reduce the weight of the insulation and the structure housing. In various embodiments, an X-ray system 100 can have any duty cycle 210. In various embodiments, the duty cycle 210 can be $1/1000$, $1/900$, $1/800$, $1/700$, $1/600$, $1/500$, $1/400$, $1/300$, $1/200$, or $1/5$ and/or any range therein. In various embodiments, the duty cycle 210 can be $1/100$, $1/90$, $1/80$, $1/70$, $1/60$, $1/50$, $1/40$, $1/30$, $1/20$, $1/10$, $1/5$, and/or any range therein. For example, in one embodiment, an X-ray system 100 has a duty cycle 210 of $1/60$. In one embodiment, an X-ray source can generate a maximum of a two second of pulsed radiation with duty cycle of $1/60$. In other words, the $1/60$ duty cycle has a pulse then a delay of 120 seconds: the next sequential pulse occurs after a 120 second delay after first pulse.

In one embodiment, an X-ray system 100 uses a two-exposure technique that uses relatively larger imaging field of view and larger digital data format than other peripheral DXA systems. In one embodiment, an X-ray system 100 is configured to measure bone densitometry with a method of quantitative imaging with resolutions of up to (or exceeding) 1% precision and accuracy of measurement of bone mass.

In one embodiment, an X-ray system 100 is configured for Dual-energy X-ray absorptiometry ("DXA") as a way of measuring Bone Mineral Density ("BMD"). In one embodiment, DXA involves two X-ray beams with differing energy levels that are directed toward a target bone for measurement. After soft tissue absorption is subtracted out of the signal, BMD can be determined from the absorption of each beam by bone. In one embodiment, the DXA scan is used to diagnose and follow osteoporosis.

In various embodiments, various techniques of dual-energy imaging and densitometry can be used. Various methods can be used to produce two distinct energetic beams. In one embodiment, an X-ray system 100 is a dual-energy imaging and densitometry system that uses a passive method that employs K-edge filtration to partition the X-ray spectrum into two energy regions. In one embodiment, an X-ray system 100 is a dual-energy imaging and densitometry system that uses an active method that makes use of two peak voltages switching (kVp switching) to alternately generate two energy spectrums. Generally, when using a dual-energy medical imaging system, motion artifacts can cause concern due to temporal interval between two energy exposures. Thus, in one embodiment, an X-ray system 100 is configured with a temporal delay that is kept as short as possible. In some embodiments, the temporal delay is 2 seconds or less, 1 second or less, 0.5 seconds or less, 0.1 seconds or less, 500 ms or less, 250 ms or less, 100 ms or less, 50 ms or less, or 10 ms or less. In certain circumstances, two primary elements that impact the temporal interval are dual-energy switching and data acquisition/recording of the first exposure data. In one embodiment, each are synchronized to function simultaneously after the first radiation exposure.

In various embodiments, an X-ray system 100 can use tube voltage switching. In one embodiment, dual-energy is produced by two different High Voltages (HV) supplied to an X-ray tube without a filter exchanger. In one embodiment, separation of two distinguished energy spectrum is interiors. In various embodiments, an X-ray system 100 can use energy filtration. In one embodiment, energy filtration uses high and energy spectrums that are obtained by placing high and low energy filters at a beam pass in front of a tube outlet window. Two advantages are a) simple X-ray power supply design; and b) fast switching time, which can be limited to less than 100 ms.

In various embodiments, an X-ray system 100 can use a combination of tube voltage switching with energy filtration. In one embodiment, a combined approach can be technically superior to achieve an optimal distinguished energy spectrum, good dual-energy separation that results in high imaging signal-to-noise ratio (SNR) and low artificial effect of beam-hardening. In one embodiment, the near mono-chromatic spectrum of dual-energy and good energy separation between high and low energies can be important for improving SNR and reduce beam-hardening of quantitative imaging. In one embodiment, SNR decreases and the effect of beam-hardening increases with increase of body size (thickness and weight), which can result in sacrifices in both precision and accuracy of quantitative measurement. However, the forearm presents one of the smallest and thinnest parts of human body for bone imaging and/or measurement, and certain adverse effects are minimized and can be corrected through post-data algorithms if necessary.

In some circumstances, the data associated with higher resolution imaging is large. Owing to large imaging data format, flat-panel detector data acquisition and recording can be time-consuming. A simple and cost-effective way to improve its efficiency and performance is incorporating detector module 300 and embedded system 150 within the imaging X-ray system 100 device.

In one embodiment, a detector 300 includes a flip-chip bonded detector chip and integrated electronics chip. Chip level integration can allow for faster electronic signal conversion and amplification. Each processed image frame can be exported via Giga-Ethernet, camera link, or via another format or means. In one embodiment, an image frame is received and processed by an embedded system chip 150 and stored in adjacent DDR3 SRDRAM. In one embodiment, the estimated processing time is about −60 ms for 48 Mbit of data.

In one embodiment, an X-ray system 100 is configured for dual-energy imaging and densitometry according to an embodiment of the present invention. In one embodiment, the X-ray system 100 comprises a filter positioning mechanism 400 configured for changing position in order to provide dual-energy imaging and densitometry for the X-ray system 100. In one embodiment, the filter positioning mechanism 400 is a filter exchanger. In one embodiment, the filter positioning mechanism 400 is a filter wheel. In one embodiment, the filter positioning mechanism 400 is a slide. In one embodiment, the filter positioning mechanism 400 is a belt. In one embodiment, the filter positioning mechanism 400 is a linear exchanger. In one embodiment, the filter positioning mechanism 400 is a rotational exchanger. In one embodiment, the filter positioning mechanism 400 is a movable system for presenting one, two, three, four, five, six, or more positions on a filter for affecting an X-ray emission from an X-ray tube 200. For example, the filter positioning mechanism 400 can comprise one or more filter positioning mechanism positions 410. In various embodiments, the filter positioning mechanism 400 can include 1, 2, 3, 4, 5, 6, or more filter positioning mechanism positions 410. In one embodiment, a filter positioning mechanism position 410 can include a high energy filter 420 configured to allow high energy X-ray transmission through the filter positioning mechanism 400. In one embodiment, the high energy filter 420 provides a high energy component for transmission through the filter positioning mechanism, and limits low energy transmission. In one embodiment, the high energy filter 420 absorbs lower energy. In one embodiment, a filter positioning mechanism position 410 can include a low energy filter 430 configured to allow low energy X-ray transmission through the filter positioning mechanism 400. In one embodiment, the low energy filter 430 provides for lower energy transmission of energy through the filter positioning mechanism. In one embodiment, the low energy filter 430 provides for second high energy transmission of energy through the filter positioning mechanism. In one embodiment, a filter positioning mechanism position 410 can include a shutter 440 for blocking X-ray transmission through the filter positioning mechanism 400. In one embodiment, a filter positioning mechanism position 410 can include a datum indicator 450 to indicate the position of the filter positioning mechanism 400 in the X-ray system 100. In one embodiment, a filter positioning mechanism position 410 can include any number of filters, shutters, indicators, or other devices, lenses, objects, interfaces, or other features for modifying the function of the X-ray system 100. In one embodiment, a filter exchanger is driven by a high-torque and high speed stepping motor. In one embodiment, a filter exchanger is configured to switch from one position to anther in 100 ms or less.

Figure 4A:
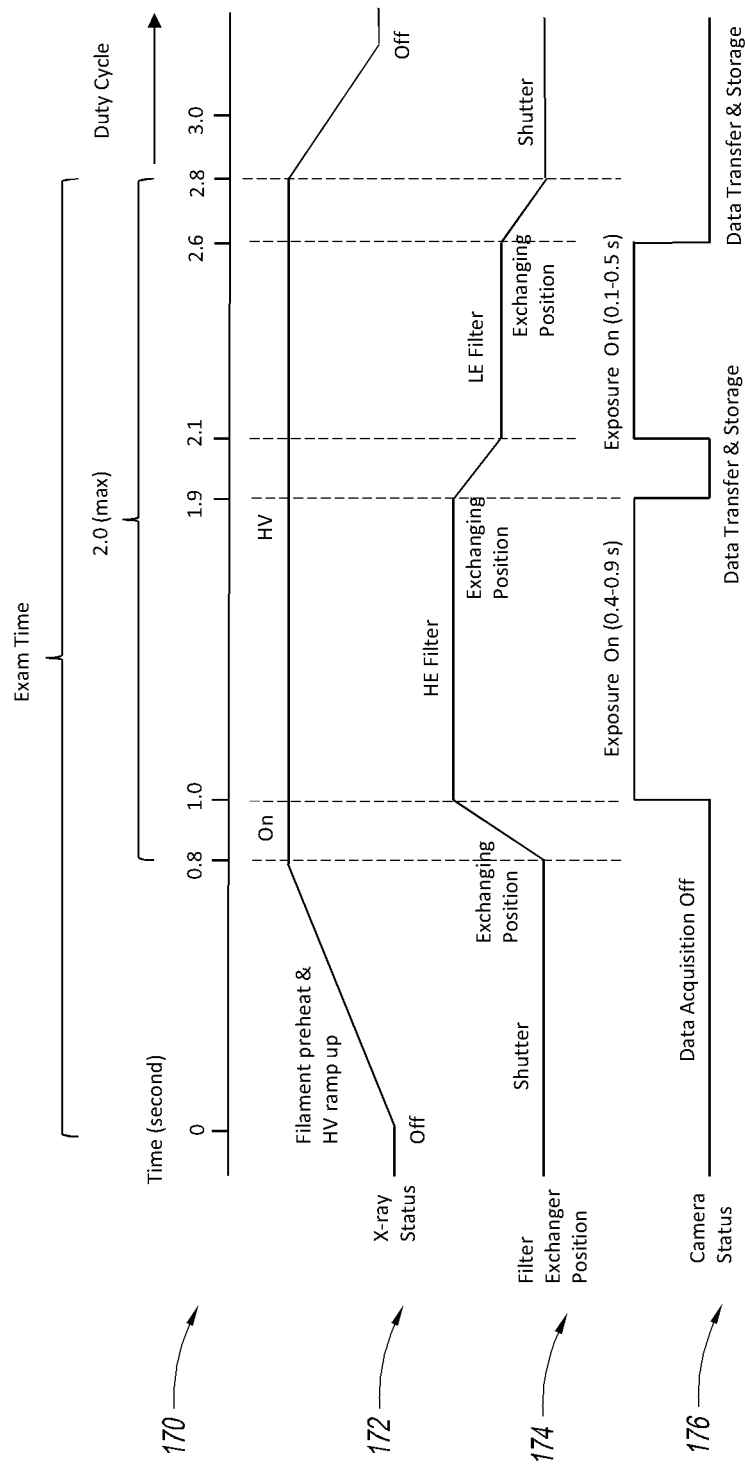
FIG. 4A is a schematic time table of various actions performed in a time period by an X-ray system with a constant high voltage (HV) X-Ray tube according to an embodiment of the present invention.
Figure 4B:
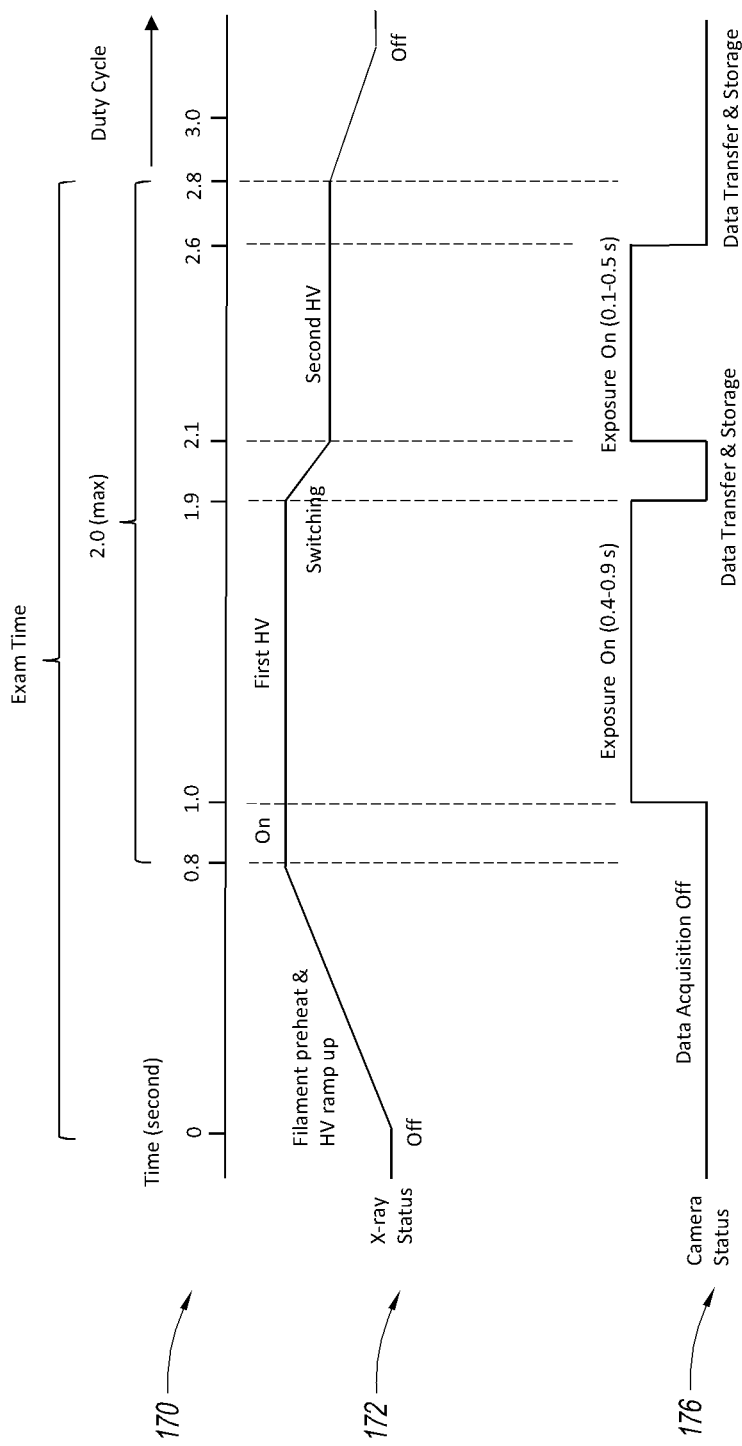
FIG. 4B is a schematic time table of various actions performed in a time period by an X-ray system with a switchable X-ray tube HV without a filter exchanger according to an embodiment of the present invention.
Figure 4C:
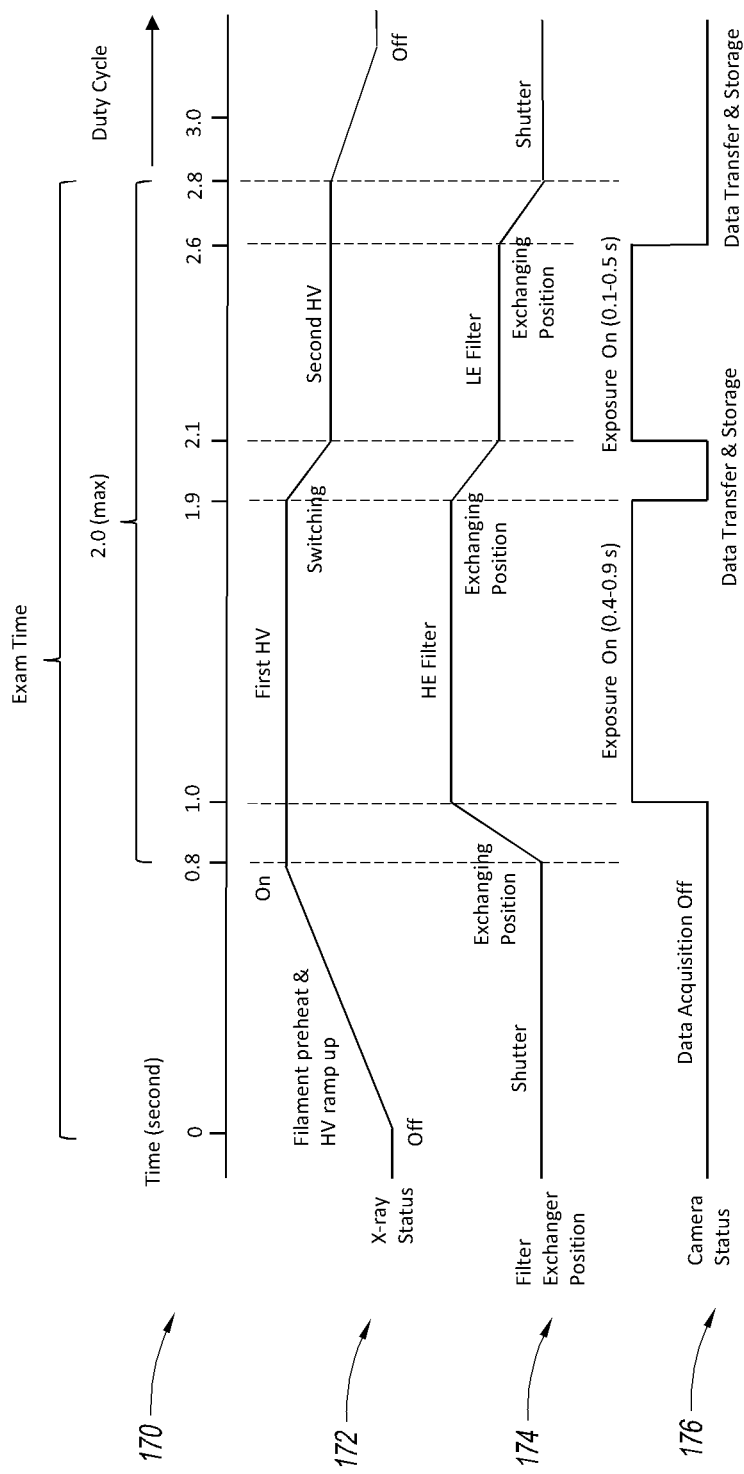
FIG. 4C is a schematic time table of various actions performed in a time period by an X-ray system with a combination of switchable HV with a filter exchanger according to an embodiment of the present invention.

In various embodiments, an X-ray system 100 configured for dual-energy imaging and densitometry. In the embodiments, specific time ranges or time values can be provided as examples, but can vary accordingly. In one embodiment, a time scale 170 shows various steps taken by an X-ray system 100. In one embodiment, a time scale 170 shows various steps taken by an X-ray system 100 with a filter positioning mechanism 400. In one embodiment, the time scale 170 provides illustrative timing sequences with a two second interval. In one embodiment, the X-ray system 100 activates X-ray tube 200, showing the X-ray status 172 (e.g. "on", "off", "HV", "LV", etc.) during the time scale 170. In some embodiments, illustrated in priority to U.S. Provisional Application No. 61/664,066, filed on Jun. 25, 2012, FIGS. 4A-4C illustrate various actions performed in a time period by various embodiments an X-ray system. U.S. Provisional Application No. 61/664,066, filed on Jun. 25, 2012, is incorporated by reference in its entirety, herein. Further, FIGS. 4A-4C and the related description from U.S. Provisional Application No. 61/664,066 is incorporated by reference herein.

In one embodiment of a constant X-ray tube High Voltage (HV) system, the X-ray status 172 has an X-ray tube 200 that turns on from an off position, ramping to "on" status between 0 to 0.2 seconds. The X-ray status 172 remains "on" until the 1.6 second mark, at which the power ramps downward to the off position during duty cycle period, and remains off until the 2.0 second mark. In various embodiments, the switching can be a step instead of a ramp, or some other profile. In one embodiment, a filter positioning mechanism position 174 is a filter exchanger position. In one embodiment, a filter positioning mechanism position 174 is a filter wheel position.

In one embodiment a constant X-ray tube High Voltage (HV) system has the X-ray system 100 activate the filter positioning mechanism 400, with the filter positioning mechanism position 174 during the time scale 170. In one embodiment, the filter positioning mechanism position 174 is at the shutter 440 at time zero, transitions between 0.2 to 0.4 seconds to a filter positioning mechanism position 174 for the high energy filter 420 between 0.4 to 0.9 seconds, transitions between 0.9 to 1.1 seconds to a filter positioning mechanism position 174 for the low energy filter 430 between 1.1 to 1.6 seconds, then returns to a shutter 440 position between 1.8 to 2.0 seconds on the time scale 170. In one embodiment, the high energy filter 420 is configured for transmission of a first high energy level. In one embodiment, the low energy filter 430 is configured for transmission of a second high energy level, wherein the second high energy level is lower than a first high energy level.

In one embodiment, a constant X-ray tube High Voltage (HV) system has the X-ray system 100 activate the data acquisition status 176 to an "on" position to acquire data during the high energy filter 420 position with an exposure time of 0.4-0.9 seconds. In one embodiment, the data acquisition status 176 switches to a "Transfer & Recording" mode at 0.9 to 1.1 seconds. The X-ray system 100 activates the data acquisition status 176 to an "on" position to acquire data during the low energy filter 430 position with an exposure time of 0.3-0.5 seconds. In one embodiment, the data acquisition status 176 switches to a "Transfer & Recording" mode at 1.6 to 2.0 seconds. In various embodiments, a data transfer and/or recording means image frame can be moved from a detector module to the SoC through Gig Ethernet and/or Camera Link and to be saved in DDR3 memory temporally. In one embodiment, data and/or an image can be saved permanently.

In one embodiment, the X-ray system 100 activates the data recording status 178 to an "on" position to transfer the acquired data to data storage at roughly the 0.9 to 1.1 second mark, after the data acquisition is off. The data recording status 178 returns to an "on" position to transfer the acquired data to data storage at roughly the 1.6 to 1.8 second mark, after the data acquisition is off. In one embodiment, the data recording or transfer to storage can occur while the data acquisition is taking place. In one embodiment, the data recording or transfer to storage can occur after the data acquisition has taken place. In some embodiments, the switching can be a step instead of a ramp, or some other profile.

In one embodiment, a switchable X-ray tube HV without a filter exchanger, has an X-ray system 100 that activates the data acquisition status 176 to an "on" position to acquire data during the high energy filter 420 position with an exposure time of 0.4-0.9 seconds. In one embodiment, the data acquisition status 176 switches to a "Transfer & Recording" mode at 0.9 to 1.1 seconds. The X-ray system 100 activates the data acquisition status 176 to an "on" position to acquire data during the low energy filter 430 position with an exposure time of 0.3-0.5 seconds. In one embodiment, the data acquisition status 176 switches to a "Transfer & Recording" mode at 1.6 to 2.0 seconds. In various embodiments, a data transfer and/or recording means image frame can be moved from a detector module to the SoC through Gig Ethernet and/or Camera Link and to be saved in DDR3 memory temporally. In one embodiment, data and/or an image can be saved permanently. In some embodiments, the switching can be a step instead of a ramp, or some other profile.

In one embodiment, a combination of switchable HV with a filter exchanger has an X-ray status 172 with the X-ray tube 200 turning on from a first HV position, ramping to the first HV position status between 0 to 0.2 seconds. In one embodiment, the X-ray status 172 remains at the first HV position until the 0.9 second mark, at which the power ramps downward to a second HV position by the 1.1 second mark, and remains at the second HV position until the 1.6 second mark. In one embodiment, the X-ray status 172 remains at the first HV position until the 0.9 second mark, at which the power ramps downward to a LV or lower voltage position by the 1.1 second mark, and remains at the LV position until the 1.6 second mark. In some embodiments, the switching can be a step instead of a ramp, or some other profile.

In one embodiment, a combination of switchable HV with a filter exchanger has the X-ray system 100 activating the filter positioning mechanism 400, showing the filter positioning mechanism position 174 during the time scale 170. In one embodiment, the filter positioning mechanism position 174 is at the shutter 440 at time zero, transitions between 0.2 to 0.4 seconds to a filter positioning mechanism position 174 for the high energy filter 420 between 0.4 to 0.9 seconds, transitions between 0.9 to 1.1 seconds to a filter positioning mechanism position 174 for the low energy filter 430 between 1.1 to 1.6 seconds, then returns to a shutter 440 position between 1.8 to 2.0 seconds on the time scale 170.

In one embodiment, a combination of switchable HV with a filter exchanger has the X-ray system 100 activate the data acquisition status 176 to an "on" position to acquire data during the high energy filter 420 position with an exposure time of 0.4-0.9 seconds. In one embodiment, the data acquisition status 176 switches to a "Transfer & Recording" mode at 0.9 to 1.1 seconds. The X-ray system 100 activates the data acquisition status 176 to an "on" position to acquire data during the low energy filter 430 position with an exposure time of 0.3-0.5 seconds. In one embodiment, the data acquisition status 176 switches to a "Transfer & Recording" mode at 1.6 to 2.0 seconds. In various embodiments, a data transfer and/or recording means image frame can be moved from a detector module to the SoC through Gig Ethernet and/or Camera Link and to be saved in DDR3 memory temporally. In one embodiment, storage is permanent.

FIGS. 4A-4C illustrate various actions performed in a time period by various embodiments of an X-ray system 100 configured for dual-energy imaging and densitometry. In the illustrated embodiments, specific time ranges or time values are provided as examples, but can vary accordingly. In one embodiment, a time scale 170 shows various steps taken by an X-ray system 100. In one embodiment, a time scale 170 shows various steps taken by an X-ray system 100 with a filter positioning mechanism 400. In one embodiment, the time scale 170 provides illustrative timing sequences with a two second interval. In one embodiment, the X-ray system 100 activates X-ray tube 200, showing the X-ray status 172 (e.g. "on", "off", "HV", "LV", etc.) during the time scale 170.

In one embodiment, a filter positioning mechanism position 174 is a filter exchanger position. In one embodiment, a filter positioning mechanism position 174 is a filter wheel position.

In one embodiment shown at FIG. 4A (constant X-ray tube High Voltage (HV)), the X-ray status 172 shows the X-ray tube 200 turns on from an off position, ramping to "on" status between 0 to 0.8 seconds. The X-ray status 172 remains "on" until the 2.8 second mark. The status can then drop to an off status. In various embodiments, the switching can be a step instead of a ramp, or some other profile.

In one embodiment shown at FIG. 4A (constant X-ray tube High Voltage (HV)), the X-ray system 100 activates the filter positioning mechanism 400, showing the filter positioning mechanism position 174 (or filter exchanger position) during the time scale 170. In one embodiment, the filter positioning mechanism position 174 is at the shutter 440 at time zero, transitions between 0.8 to 1.0 seconds to a filter positioning mechanism position 174 for the high energy filter 420 between 1.0 to 1.9 seconds, transitions between 1.9 to 2.1 seconds to a filter positioning mechanism position 174 for the low energy filter 430 between 2.1 to 2.6 seconds, then returns to a shutter 440 position between 2.6 to 2.8 seconds on the time scale 170. In one embodiment, the high energy filter 420 is configured for transmission of a first high energy level. In one embodiment, the low energy filter 430 is configured for transmission of a second high energy level, wherein the second high energy level is lower than a first high energy level.

In one embodiment, a data acquisition status 176 is a camera status 176.

In one embodiment shown at FIG. 4A (constant X-ray tube High Voltage (HV)), the X-ray system 100 activates the data acquisition status 176 to an "on" position to acquire data during the high energy filter 420 position with an exposure time of 0.4-0.9 seconds. In one embodiment, the data acquisition status 176 switches to a "Transfer & Recording" mode at 1.9 to 2.1 seconds. The X-ray system 100 activates the data acquisition status 176 to an "on" position to acquire data during the low energy filter 430 position with an exposure time of 0.1-0.5 seconds. In one embodiment, the data acquisition status 176 switches to a "Transfer & Recording" mode at 2.6 to 2.8 seconds. In various embodiments, a data transfer and/or recording means image frame can be moved from a detector module to the SoC through Gig Ethernet and/or Camera Link and to be saved in DDR3 memory temporally. In one embodiment, data and/or an image can be saved permanently.

In one embodiment shown at FIG. 4B (switchable X-ray tube HV without a filter exchanger), the X-ray status 172 shows the X-ray tube 200 turns on from a first HV position, ramping to the first HV position status between 0 to 0.8 seconds. In one embodiment, the X-ray status 172 remains at the first HV position until the 1.9 second mark, at which the power ramps downward to a second HV position by the 2.1 second mark, and remains at the second HV position until the 2.8 second mark. In one embodiment, the X-ray status 172 remains at the first HV position until the 1.9 second mark, at which the power ramps downward to a LV or lower voltage position by the 2.1 second mark, and remains at the LV position until the 2.8 second mark. In other embodiments, the switching can be a step instead of a ramp, or some other profile.

In one embodiment shown at FIG. 4B (switchable X-ray tube HV without a filter exchanger), the X-ray system 100 activates the data acquisition status 176 to an "on" position to acquire data during the high energy filter 420 position with an exposure time of 0.4-0.9 seconds. In one embodiment, the data acquisition status 176 switches to a "Transfer & Recording" mode at 1.9 to 2.1 seconds. The X-ray system 100 activates the data acquisition status 176 to an "on" position to acquire data during the low energy filter 430 position with an exposure time of 0.1-0.5 seconds. In one embodiment, the data acquisition status 176 switches to a "Transfer & Recording" mode at 2.6 to 2.8 seconds. In various embodiments, a data transfer and/or recording means image frame can be moved from a detector module to the SoC through Gig Ethernet and/or Camera Link and to be saved in DDR3 memory temporally. In one embodiment, data and/or an image can be saved permanently. In some embodiments, the switching can be a step instead of a ramp, or some other profile.

In one embodiment shown at FIG. 4C (combination of switchable HV with a filter exchanger), the X-ray status 172 shows the X-ray tube 200 turns on from a first HV position, ramping to the first HV position status between 0 to 0.8 seconds. In one embodiment, the X-ray status 172 remains at the first HV position until the 1.9 second mark, at which the power ramps downward to a second HV position by the 2.1 second mark, and remains at the second HV position until the 2.8 second mark. In one embodiment, the X-ray status 172 remains at the first HV position until the 1.9 second mark, at which the power ramps downward to a LV or lower voltage position by the 2.1 second mark, and remains at the LV position until the 2.8 second mark. In some embodiments, the switching can be a step instead of a ramp, or some other profile.

In one embodiment shown at FIG. 4C (combination of switchable HV with a filter exchanger), the X-ray system 100 activates the filter positioning mechanism 400, showing the filter positioning mechanism position 174 during the time scale 170. In one embodiment, the filter positioning mechanism position 174 is at the shutter 440 at time zero, transitions between 0.8 to 1.0 seconds to a filter positioning mechanism position 174 for the high energy filter 420 between 1.0 to 1.9 seconds, transitions between 1.9 to 2.1 seconds to a filter positioning mechanism position 174 for the low energy filter 430 between 2.1 to 2.6 seconds, then returns to a shutter 440 position between 2.6 to 2.8 seconds on the time scale 170.

In one embodiment shown at FIG. 4C (combination of switchable HV with a filter exchanger), the X-ray system 100 activates the data acquisition status 176 to an "on" position to acquire data during the high energy filter 420 position with an exposure time of 0.4-0.9 seconds. In one embodiment, the data acquisition status 176 switches to a "Transfer & Recording" mode at 1.9 to 2.1 seconds. The X-ray system 100 activates the data acquisition status 176 to an "on" position to acquire data during the low energy filter 430 position with an exposure time of 0.1-0.5 seconds. In one embodiment, the data acquisition status 176 switches to a "Transfer & Recording" mode at 2.6 to 2.8 seconds. In various embodiments, a data transfer and/or recording means image frame can be moved from a detector module to the SoC through Gig Ethernet and/or Camera Link and to be saved in DDR3 memory temporally. In one embodiment, storage is permanent.

Figure 4D:
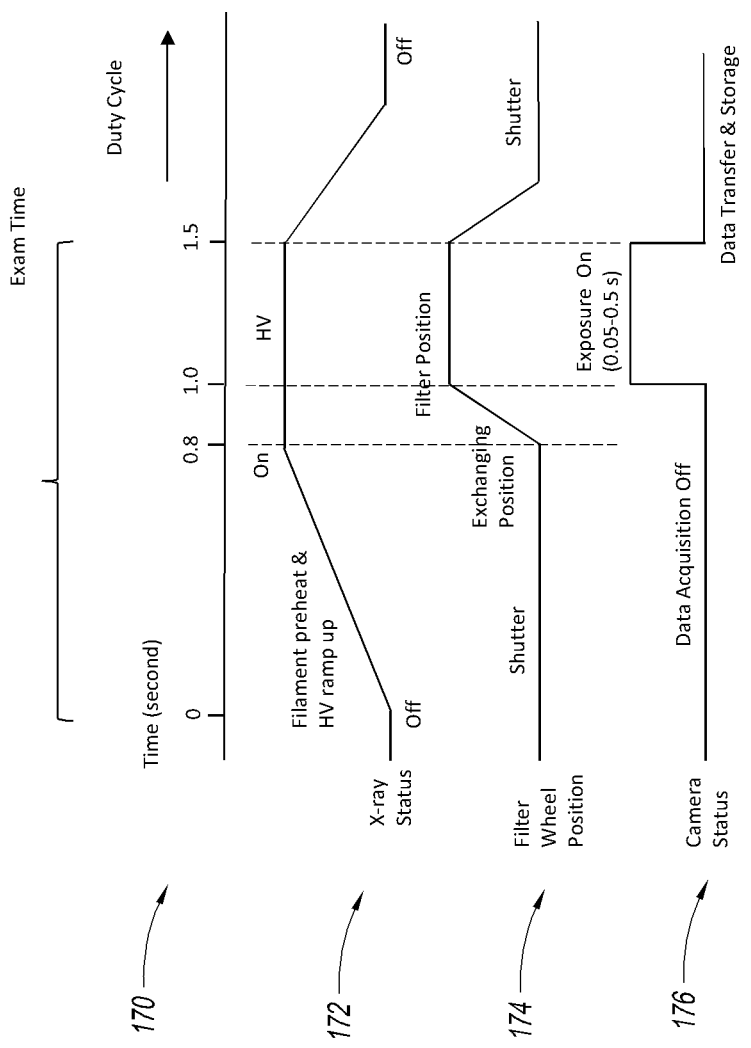
FIG. 4D is a schematic time table of various actions performed in a time period by an X-ray system with a single-energy radiographic operation according to an embodiment of the present invention.
Figure 4E:
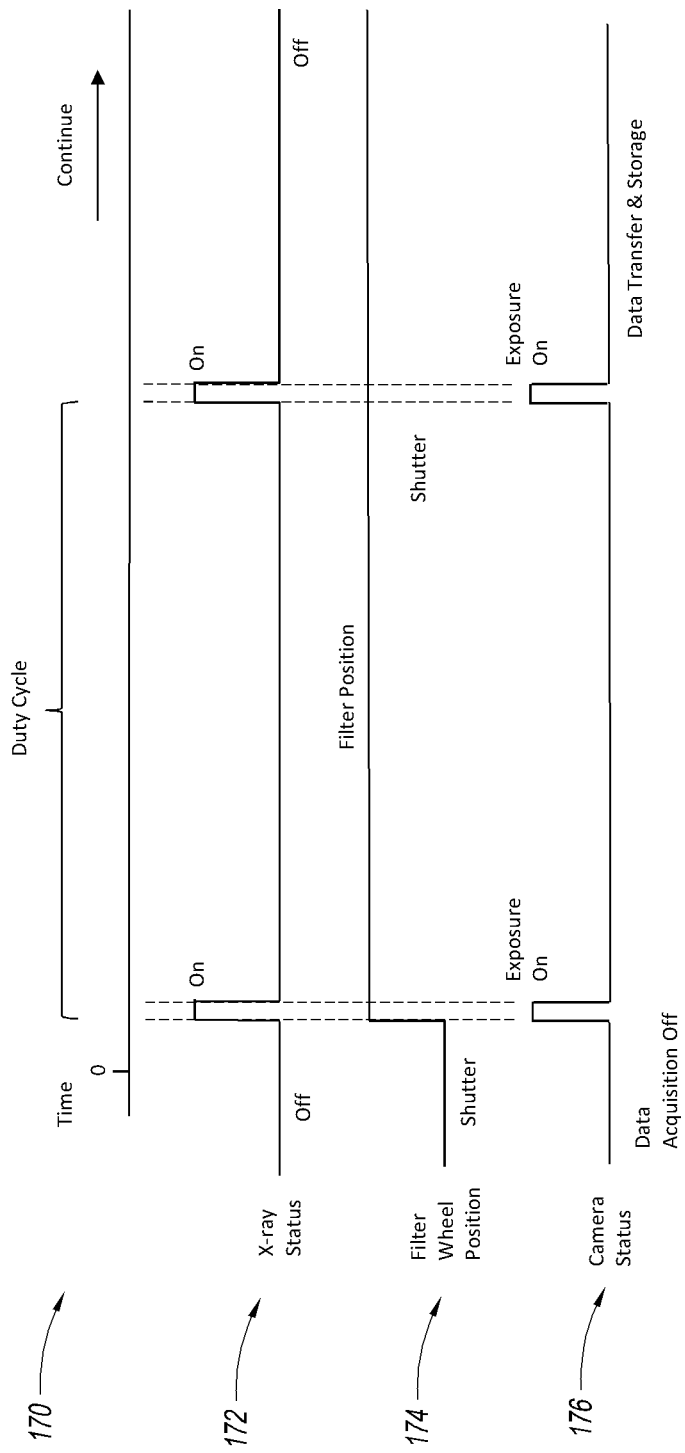
FIG. 4E is a schematic time table of various actions performed in a time period by an X-ray system with a single-energy, continued pulse exposure operation according to an embodiment of the present invention.

FIGS. 4D-4E illustrate various actions performed in a time period by various embodiments of an X-ray system 100 configured for single-energy radiography for imaging and densitometry. In the illustrated embodiments, specific time ranges or time values are provided as examples, but can vary accordingly. In one embodiment, a time scale 170 shows various steps taken by an X-ray system 100. In one embodiment, a time scale 170 shows various steps taken by an X-ray system 100 with a filter positioning mechanism 400. In one embodiment, the time scale 170 provides illustrative timing sequences. In one embodiment, the X-ray system 100 activates X-ray monoblock 200, showing the X-ray status 172 (e.g. "on", "off", "HV", "LV", etc.) during the time scale 170, with a filter wheel position 174 and a camera status 176.

Figure 10:
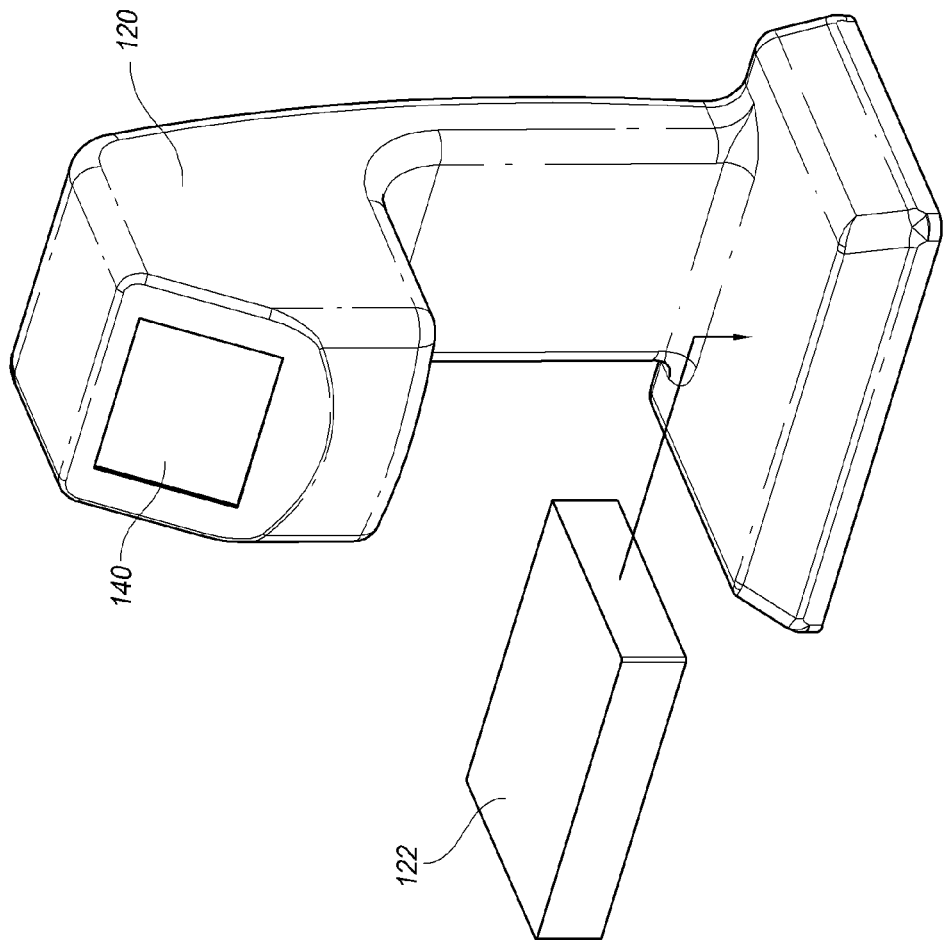
FIG. 10 is an isometric front view of the housing of the X-Ray system according to FIG. 9A.
Figure 12:
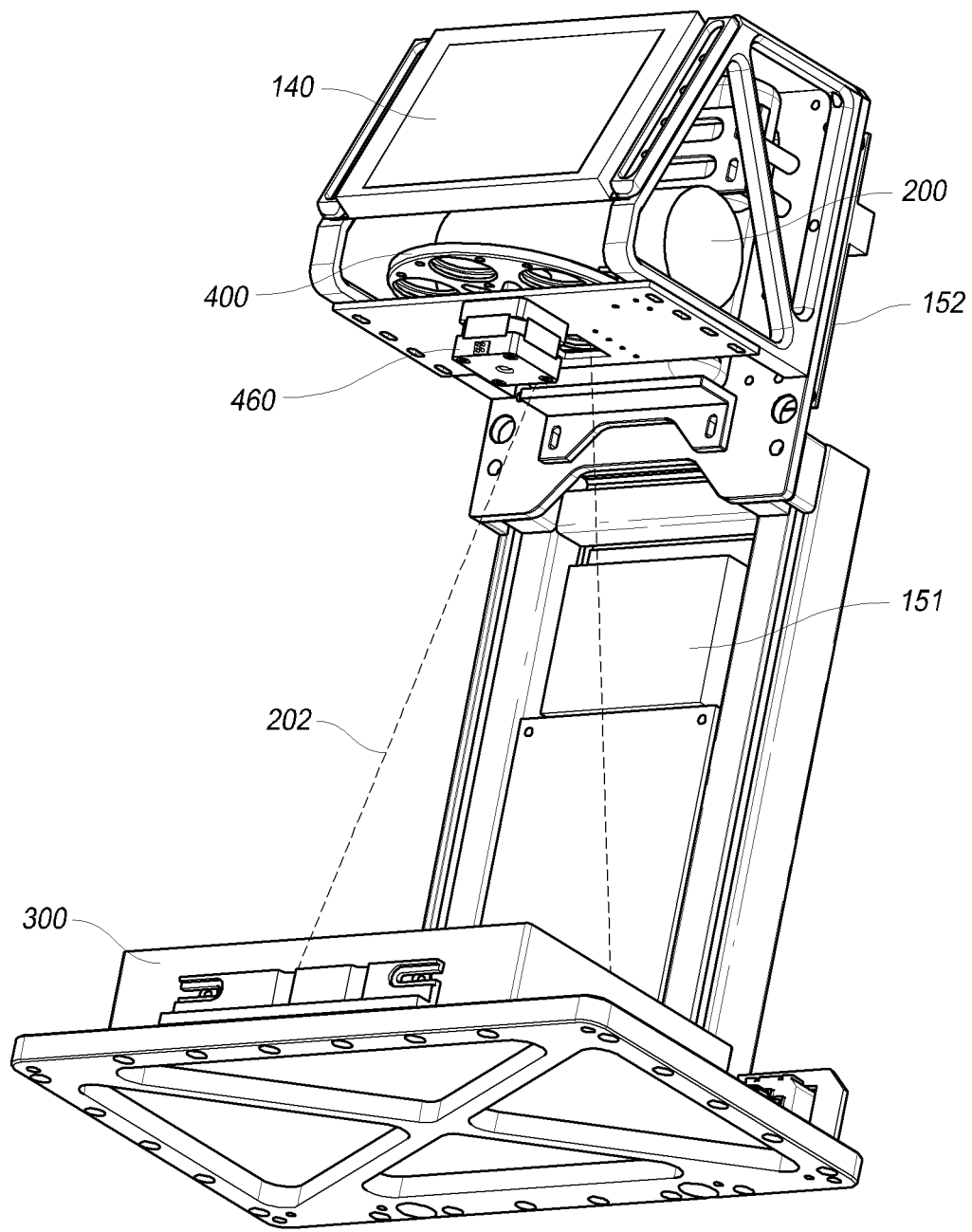
FIG. 12 is an isometric view of the X-Ray system according to FIG. 9A.
Figure 13:
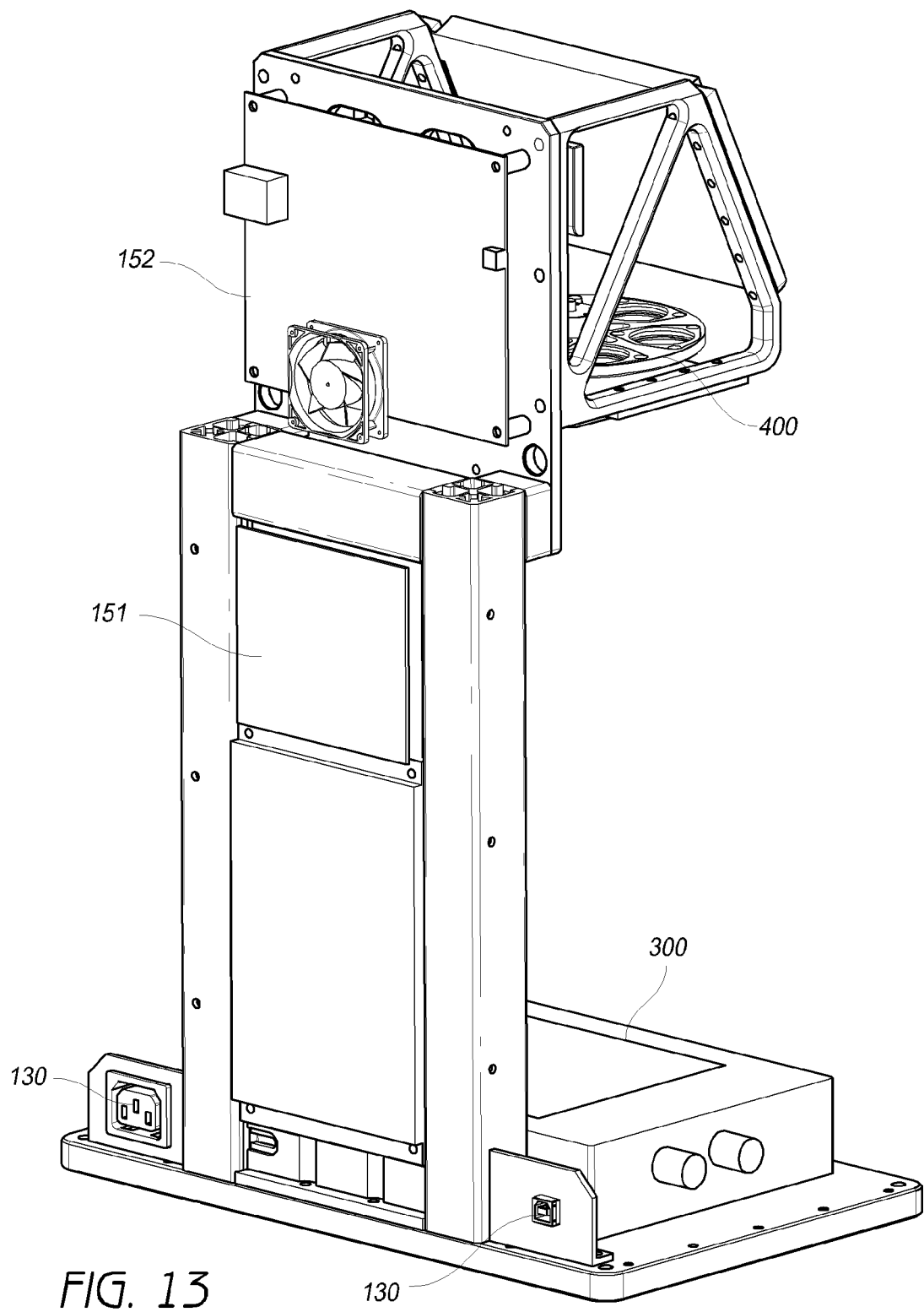
FIG. 13 is an isometric rear view of the X-Ray system according to FIG. 9A.

In one embodiment, such as shown at FIG. 10, an optional anti-scattering grid 122 can be positioned on top of a detector panel 300. In one embodiment, anti-scattering grid 122 is used in single energy high resolution radiography. In one embodiment, anti-scattering grid 122 is not used during dual-energy operation (i.e. dual-energy bone densitometry).

In one embodiment shown at FIG. 4D (an X-ray system with a single-energy radiographic operation, single exposure), the X-ray status 172 shows the X-ray monoblock 200 turns on from an off position, ramping to "on" status between 0 to 0.8 seconds. The X-ray status 172 remains "on" until the 1.5 second mark, at which the power ramps downward to the off position by the 1.5 second mark. In various embodiments, the switching can be a step instead of a ramp, or some other profile.

In one embodiment shown at FIG. 4D (X-ray system with a single-energy radiographic operation, single exposure), the X-ray system 100 activates the filter positioning mechanism 400, showing the filter wheel position 174 during the time scale 170. In one embodiment, the filter wheel position 174 is at the shutter 440 at time zero, transitions between 0.8 to 1.0 seconds to a filter wheel position 174 for the desirable energy filter 420 between 1.0 to 1.5 seconds, then transitions to a filter wheel position 174 for the low energy filter. In one embodiment, the high energy filter 420 is configured for transmission of a first high energy level.

In one embodiment shown at FIG. 4D (X-ray system with a single-energy radiographic operation, single exposure), the X-ray system 100 activates the camera status 176 to an "on" position to acquire data during the high energy filter 420 position with an exposure time of 5-100 ms. In one embodiment, x-ray pulse is activated for 5 ms. In one embodiment, x-ray pulse is activated for 10 ms. In one embodiment, x-ray pulse is activated for 20 ms. In one embodiment, x-ray pulse is activated for 30 ms. In one embodiment, x-ray pulse is activated for 40 ms. In one embodiment, x-ray pulse is activated for 50 ms. In one embodiment, x-ray pulse is activated for 100 ms. In one embodiment, the camera status 176 switches to a "Transfer & Recording" mode at 0.05-1.0 seconds. The X-ray system 100 activates the camera status 176 to an "on" position to acquire data during the low energy filter 430 position. In one embodiment, the camera status 176 switches to a "Transfer & Storing" mode. In various embodiments, a data transfer and/or storing means image frame can be moved from a detector module to the SoC through Gig Ethernet and/or Camera Link and to be saved in DDR3 memory temporally. In one embodiment, data and/or an image can be saved permanently.

In one embodiment, a single energy radiography, continued pulse exposure system can operate by switching the filter wheel to a desirable position from a shutter position. The X-ray can be set to a desirable high voltage level. In one embodiment, a detector exposure is active for 0.05-0.1 seconds. The data can be saved and the X-ray switched off. In various embodiments, the system can perform a duty cycle with a ratio of exposure duration and down-time duration, such as ½, ⅕, 1/10, 1/20, 1/30, or 1/60, or otherwise. In various embodiments, the X-ray voltage level, detector exposure, and saving data and turning the X-ray off can be repeated. In various embodiments, the process continues as long as needed.

In one embodiment shown at FIG. 4E (single energy radiography, continued pulse exposure), the X-ray status 172 shows the X-ray monoblock 200 turns on for a step-wise "on" position, which can be repeated.

In one embodiment shown at FIG. 4E (single energy radiography, continued pulse exposure), the X-ray system 100 activates the camera status 176 to an "on" position to acquire data during the X-ray status 172 "on" position.

Figure 4F:
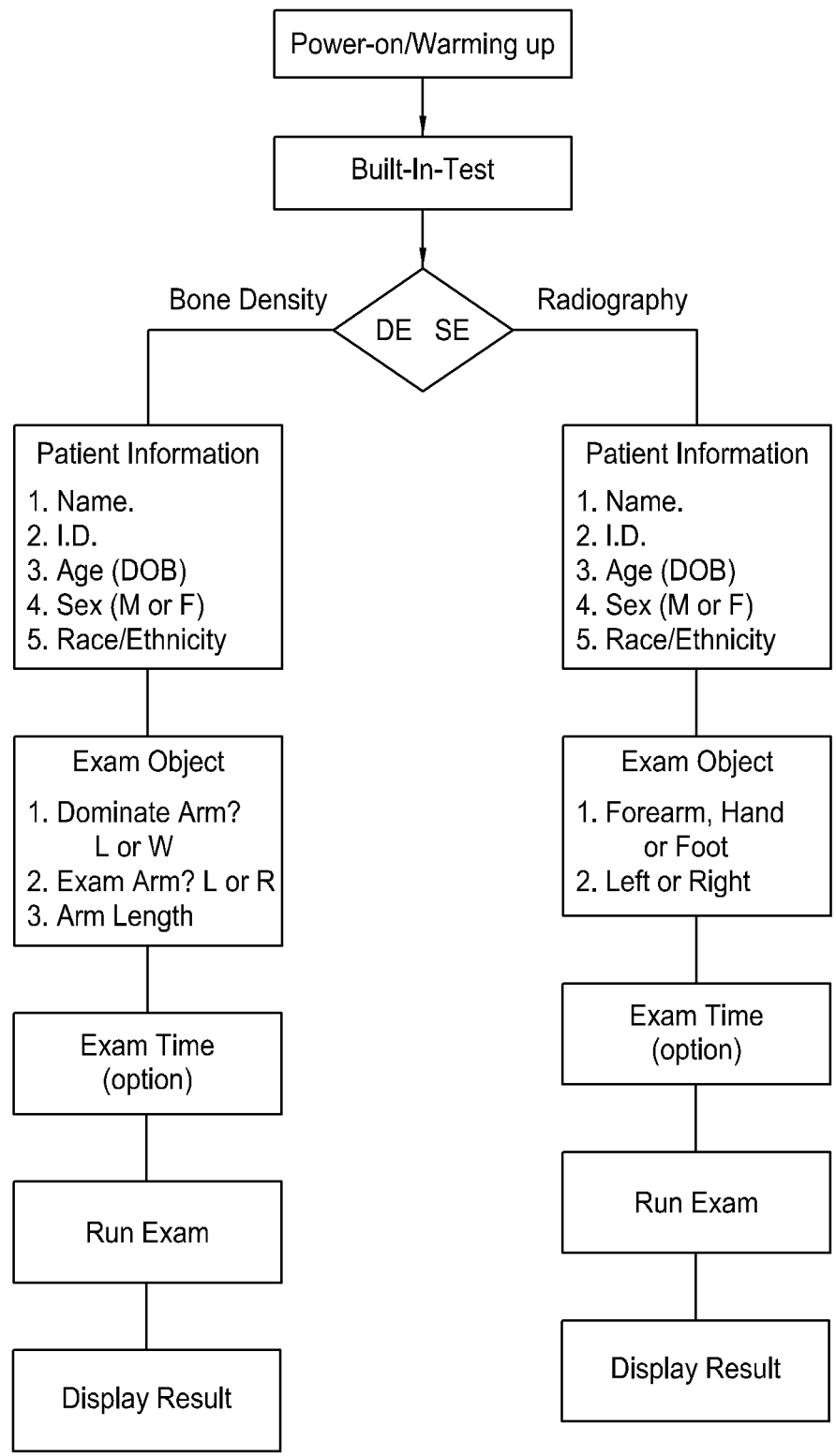
FIG. 4F is a flow chart of various steps performed by an X-ray system according to an embodiment of the present invention.

In one embodiment, a flow chart of various steps performed by an X-ray system according to an embodiment of the present invention are shown at FIG. 4F.

Figure 5A:
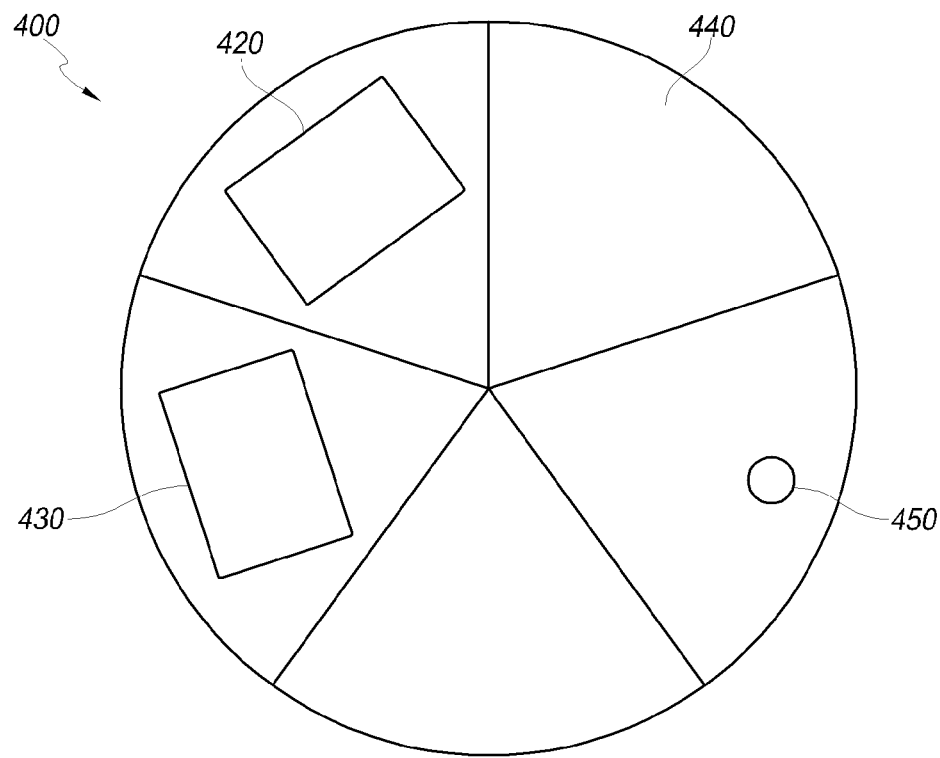
FIG. 5A is a schematic top view of a filter positioning mechanism according to an embodiment of the present invention.
Figure 5B:
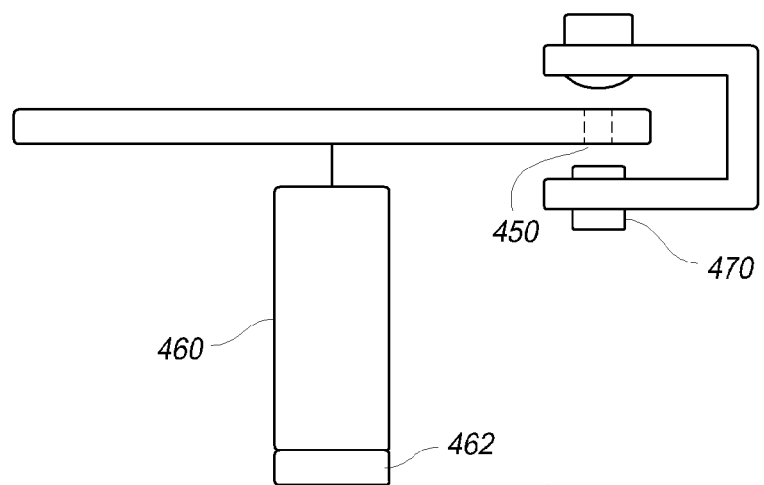
FIG. 5B is a schematic side view of the filter positioning mechanism according to FIG. 5A.

FIGS. 5A-5B illustrate a filter positioning mechanism 400 according to an embodiment of the present invention. In one embodiment, a filter positioning mechanism 400 has filter positioning mechanism positions 410 that can include a high energy filter 420, and a low energy filter 430. In one embodiment, a filter positioning mechanism 400 has filter positioning mechanism positions 410 that can include a high energy filter 420, a low energy filter 430, and a shutter 440. In one embodiment, a filter positioning mechanism 400 has filter positioning mechanism positions 410 that can include a high energy filter 420, a low energy filter 430, a shutter 440 and a datum indicator 450. In one embodiment, the filter positioning mechanism 400 is positioned with a motor. In one embodiment, the filter positioning mechanism 400 is rotatably or linearly positioned with a stepper motor 460. In one embodiment, a motor sensor 462 detects the position of the motor 460. In one embodiment, a filter positioning mechanism sensor 470 detects the position of the filter positioning mechanism 400. In one embodiment, the filter positioning mechanism sensor 470 interacts with a datum indicator 450 on the filter positioning mechanism 400 to register a position. In one embodiment, the datum indicator 450 is a hold in the filter positioning mechanism and the filter positioning mechanism sensor 470 comprises an emitter/detector sensor pair (such as an LED and a photo diode) for sensing when the datum indicator 450 passes over or between the filter positioning mechanism sensor 470. In one embodiment, a beam collimator 480 made of lead is used to block unused x-rays that falls outside the field of view of image receptor.

Figure 6:
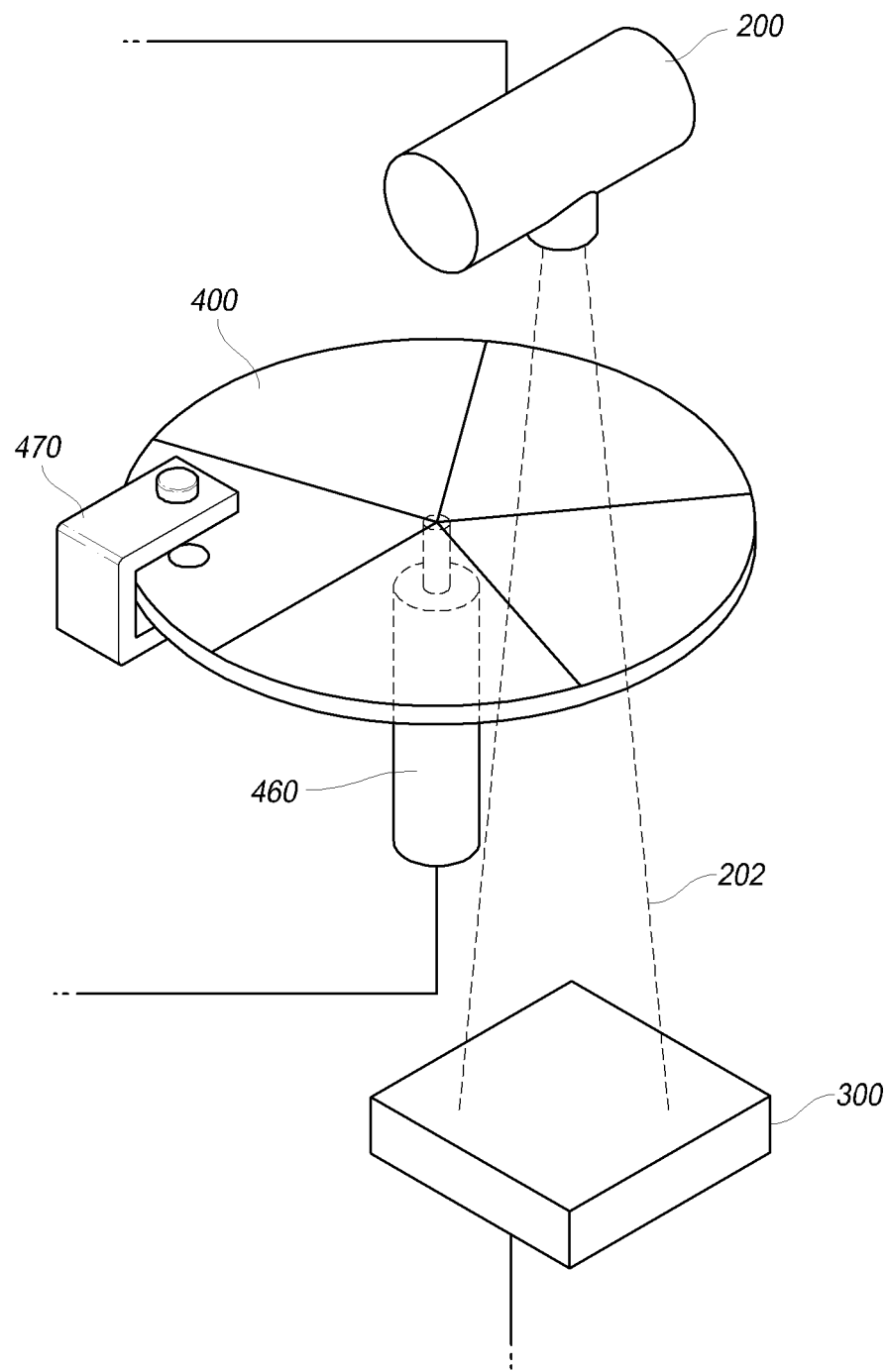
FIG. 6 is an isometric view of the filter positioning mechanism with an X-ray tube according to FIG. 5A.

FIG. 6 illustrates the filter positioning mechanism 400 with an X-ray tube 200 according to FIG. 5A, according to an embodiment of an X-ray system 100. In one embodiment, the X-ray tube 200 emits an X-ray beam 202 toward an imaging detector 300. In one embodiment, the X-ray beam 202 is a cone beam.

Figure 7:
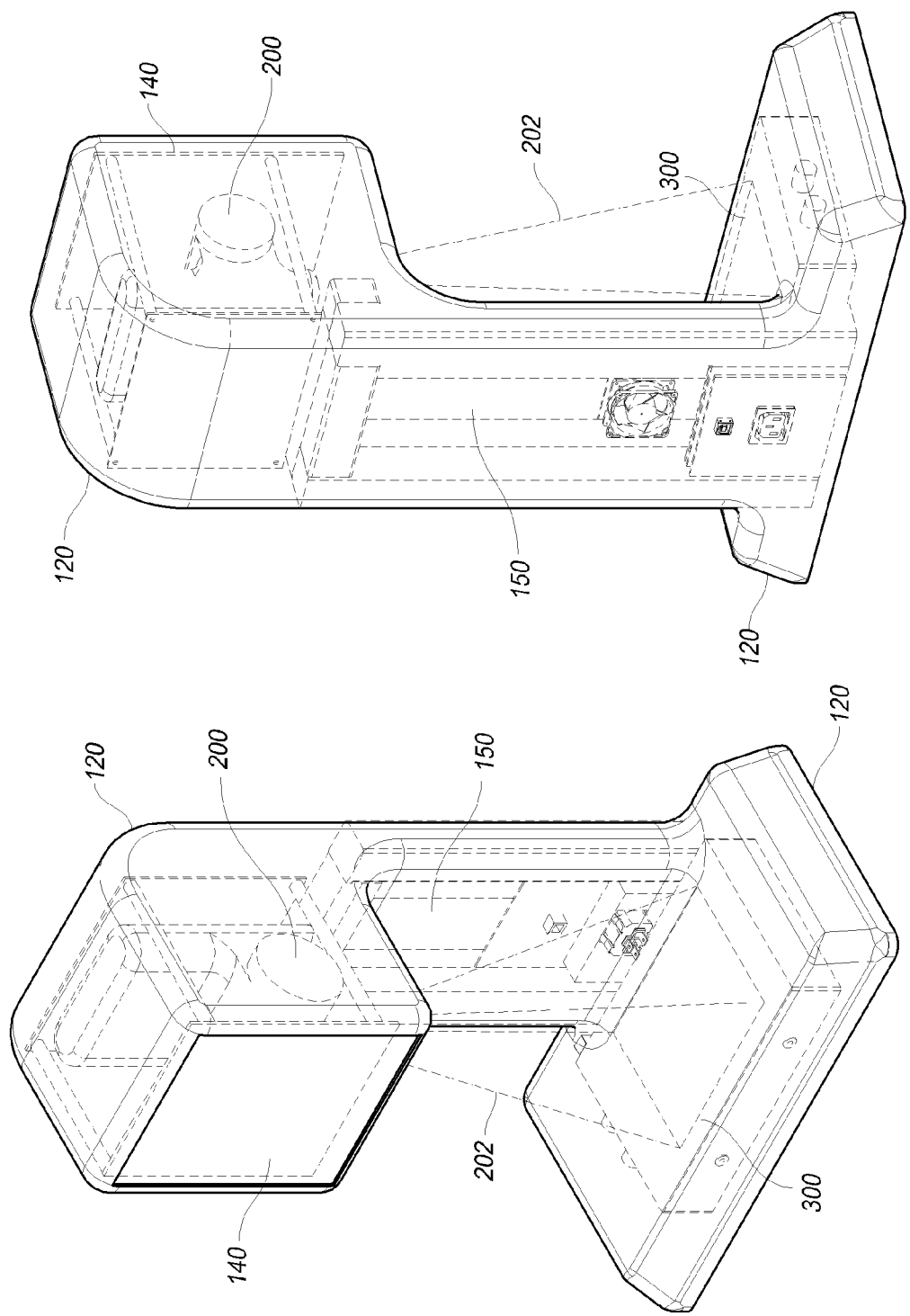
FIG. 7 is an isometric front and back view of an X-ray system according to an embodiment of the present invention.
Figure 8B:
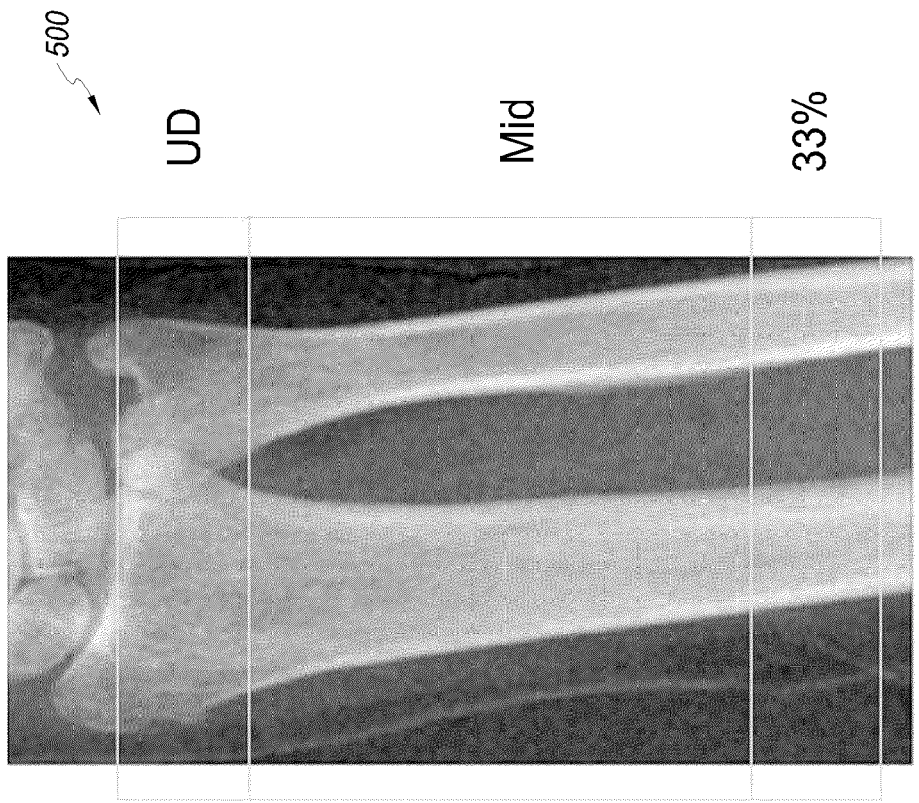
FIG. 8B is a bone density image of the forearm by the X-ray system according to FIG. 8A.
Figure 8A:
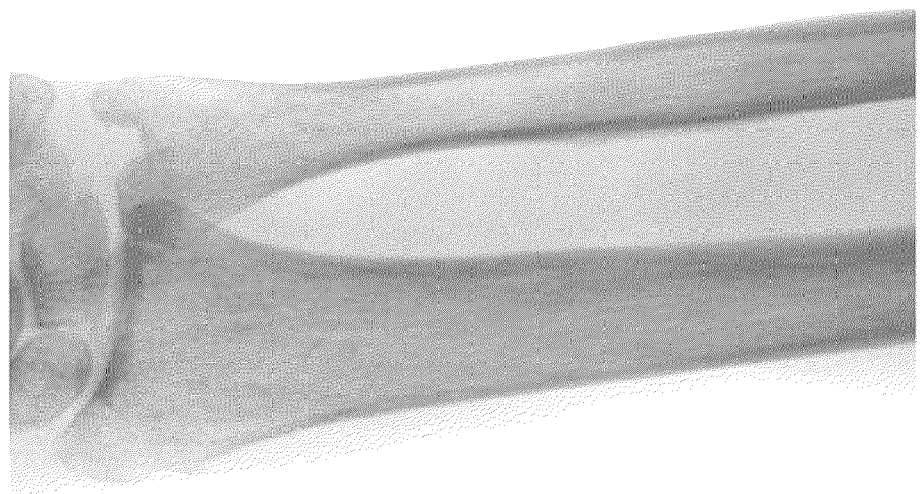
FIG. 8A is a radiographic image of a forearm by an X-ray system according to an embodiment of the present invention.

FIG. 7 illustrates an X-ray system 100 according to an embodiment of the present invention. The X-ray system 100 comprises a housing 120, a printed circuit board embedded system 150, an X-ray tube 200 configured to emit a cone X-ray beam 202, a LCD/touch screen interface 140, and an X-ray detector 300. The housing 120 includes a fan, power plug outlet, and any number of connectors 130. The X-ray system 100 is configured for placement of a bone in a patient over the detector 300 and under the X-ray monoblock 200. For example, in one embodiment, a forearm 500 (not illustrated) is placed in the X-ray system 100 for dual-energy imaging and densitometry. In one embodiment, an X-ray system 100 is configured for measurement of the ultra-distal ("UD") radius and/or at the 33% radius for a dominate arm, a non-dominate arm, or both. FIG. 8A is a radiographic image of a forearm 500 by an X-ray system 100 according to an embodiment of the present invention. FIG. 8B is a bone density image of the forearm 500 by the X-ray system 100 according to FIG. 8A.

Figure 9C:
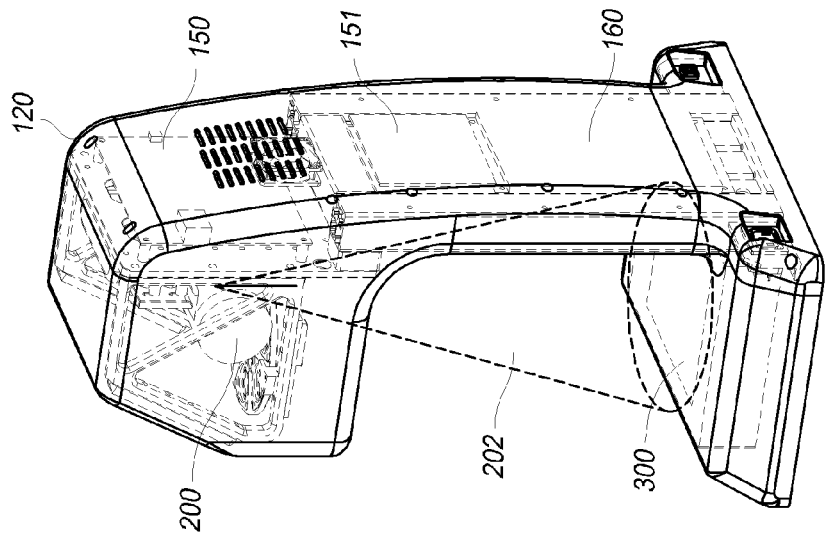
FIG. 9C is an isometric back view of the X-Ray system according to FIG. 9A.
Figure 9B:
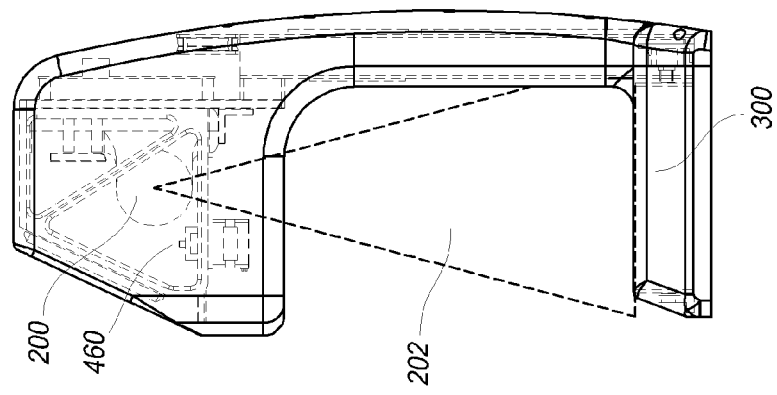
FIG. 9B is a side view of the X-Ray system according to FIG. 9A.
Figure 9A:
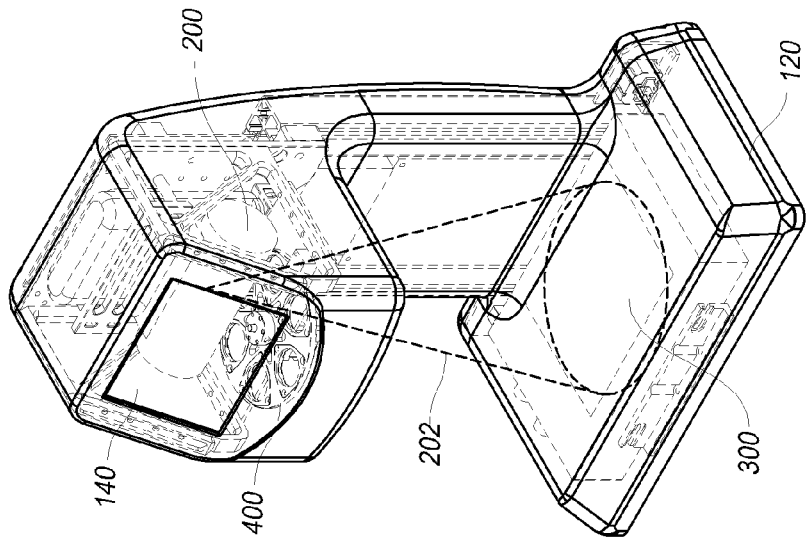
FIG. 9A is an isometric front view of an X-ray system according to an embodiment of the present invention.
Figure 11:
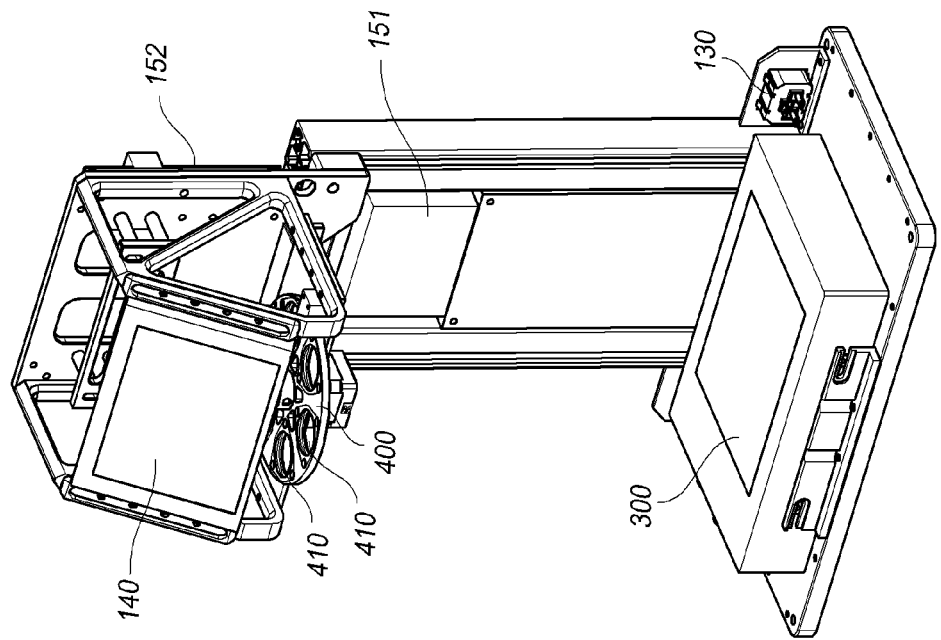
FIG. 11 is an isometric front view of the X-Ray system according to FIG. 9A.

FIGS. 9A-9C illustrate an X-ray system 100 according to the embodiment in FIG. 7 with a filter positioning mechanism 400 according to an embodiment of the present invention. In one embodiment, the X-ray system 100 The X-ray system 100 comprises a housing 120, a printed circuit board embedded system 150, an X-ray tube 200 configured to emit a cone X-ray beam 202, a LCD/touch screen interface 140, an X-ray detector 300, a filter positioning mechanism 400 and a motor 460. FIGS. 10-13 illustrate the embodiment of the X-ray system 100 of FIGS. 9A-9C.

In one embodiment of the present invention, a portable imaging and bone density monitoring X-ray system 100 is an ultra-compact and light-weight dual-energy imaging device is configured to image a bone site and estimate bone density using an X-ray source with a high resolution/speed imaging detector. In various embodiments, the bone site can be a peripheral bone site, such as (but not limited to) an arm, a forearm, a hand, a wrist, a finger, a leg, a shin, an ankle, a heel, a foot, a toe, or other body site.

In one embodiment, an X-ray system 100 includes a flat-panel detector 300, an X-ray source 200 with system integration using embedded system 150 design (including incorporating a microprocessor, touch-screen 140 and USB connection 132 and/or a wireless interfaces 134. In one embodiment, an X-ray system 100 includes a single pulsed X-ray source (for less than 2 seconds) to acquire dual-energy imaging data. The flat panel detector 300 module is integrated with internal high-speed electronics and various connectors 130, such as (but not limited to) Ethernet and/or camera links. In one embodiment, an X-ray system 100 includes "System-on-chip" (SoC)/"System-on-board" (SoB 152) technology to integrate system (dual-energy exposures, motor control, high-speed data transfer and storage, etc.) In one embodiment, an X-ray system 100 is similar to a pDXA device but also can be served as high resolution imaging device or small field radiography. In one embodiment, an X-ray system 100 uses dual-energy methods to measure bone density at forearm, from Ultra-distal (UD) to 33% of forearm. It can take radiographic imaging of a forearm or a hand or a foot (with the option of single or dual-energy imaging). It can take radiographic imaging of a small animal (with the option of single or dual-energy imaging).

In one embodiment, an X-ray system 100 includes a low-weight X-ray monoblock 200 and pulsed X-ray radiation emitted in an X-ray beam 202. In one embodiment, the X-ray tube 200 source may be a monoblock without additional cooling utility. In one embodiment, the X-ray tube 200 source has a fixed tube voltage in the range of 70-80 kV and fixed tube current in the range of 2-5 mA. In one embodiment, the X-ray tube 200 source has a variable/adjustable tube voltage from 40 to 80 kV and fixed tube current in the range of 2-5 mA. In one embodiment, the X-ray tube 200 source has a pulsed width with a 2 second (max) and a duty cycle of 1/60. In one embodiment, the X-ray tube 200 source has a voltage rise-time of less than 200 ms from 10% to 90% of rated voltage. In one embodiment, the X-ray tube 200 source has a focal spot size: less than 0.4 mm. In one embodiment, the X-ray tube 200 source emits a beam 202 with cone beam geometry. In one embodiment, an X-ray system 100 is light weight, with a total weight for the X-ray monoblock 200 and the control board of less than 5 pounds.

In one embodiment, an X-ray system 100 includes a high resolution flat panel X-ray detector module 300. In one embodiment, the flat panel detector 300 has a pixel size of 75-150 micron pitch to pitch. In various embodiments, the active area can be approximately 13×13 cm or 15×12 cm. In various embodiments, the active area is large enough to image a forearm from UD to 33% of radius. In one embodiment, the numbers of pixels is approximately 1.5 million pixels for 140 micron and ~3 million pixels for 75 micron. In one embodiment, the digital output is 14 or 16 bit/pixel. In one embodiment, the image data output is 16 bit/pixel×3 million pixels=48 Mbits. In one embodiment, flat panel detector module has a Giga-bit Ethernet for data transmission. For instance, a transmission time of 80% of one set of 48 Mbits image is 60 ms (=48/0.8). In one embodiment, flat panel detector module provides a Camera Link for data transmission. In one embodiment, the X-ray conversion can use a CsI scintillator, a Gadox scintillator, or other scintillator.

In one embodiment, an X-ray system 100 includes an embedded system 150 using a System-on-Board (SoB 152) 152 design powered by System-on-Chip (SoC) technology. In one embodiment, an X-ray system 100 uses a SoB 152 with a custom-designed PCB (Printed Circuit Board) powered by System-on-Chip (SoC) technology. In one embodiment, the PCB is a SoB 152.

In one embodiment, an X-ray system 100 includes a SoB 152 that contains a PBGA IC (SoC or System-on-Chip) that includes an internal microprocessor (for example, operating a 500 MHz, 700 MHz, or other frequencies) for system control and operating system (OS) support. In one embodiment, an X-ray system 100 includes a SoB 152 with low power consumption, such as at 7 mW standby power and 700 mW active power. In one embodiment, an X-ray system 100 includes a SoB 152 with integrated 3-D graphics and a touch screen controller 140. In one embodiment, an X-ray system 100 includes a SoB 152 with fast network connectivity, which can include a Giga-bit Ethernet controller, DDR3 SDRAM interface and/or a USB controller. In one embodiment, an X-ray system 100 includes a SoB 152 with on-chip peripherals, such as for connection to sensors, actuators, devices and cost optimization. In one embodiment, an X-ray system 100 includes a SoB 152 with a PCB size (5"×6") capable of high-speed/high band-width PCB layout to accommodate Giga-bit Ethernet and/or DDR3 data rates. In one embodiment, an X-ray system 100 includes a SoB 152 can have DDR3 SDRAM IC (adjacent to SoC, allowing for data to be transferred and stored quickly (for instance to acquire and save one set of image frame in less than 100 miliseconds). In one embodiment, an X-ray system 100 includes a SoB 152 with one or more, or any combination of, a flash memory integrated circuit, a stepping motor micro-controller, stepping motor positioning circuitry/IC, power supply converter/regulator, and/or a Wi-Fi/blue-tooth module. Note: DDR3 stands for (Double Data Rate, type 3). Note: SDRAM stands for (Synchronous Dynamic Random Access Memory).

In one embodiment, an X-ray system 100 is configured for dual-energy filtration. In one embodiment, the X-ray system 100 has a filter exchanger assembly (or filter positioning mechanism 400) implemented by a stepping motor and positioning mechanism. In one embodiment, the filter positioning mechanism 400 comprises one position for a high energy filter 420 that can provide a high energy component above 40-50 kV. In one embodiment, the high energy filter 420 includes Copper (Cu)+Tin (Sn) and/or Copper (Cu)+Rhodium (Rh).

In one embodiment, the filter positioning mechanism 400 comprises one position for a low energy filter 430 that can provide filtration of high energy component below 40-50 kV. In one embodiment, the low energy filter 430 includes Aluminum (Al)+one type of material having one K-edge absorption around 40 kV. In various embodiments, the K-edge materials can be one or more of Cerium (Ce, K-edged at 40 kV), Samarium (Sm, K-edged at 46.8 kV), Gadolinium (Gd, K-edged at 50.2 kV), Barium (Ba, K-edged at 37.45 kV).

In one embodiment, the filter positioning mechanism 400 comprises one position for a shutter 440 (permanently closed) position to block radiation for safety, non-exam time, etc. In any embodiment, the filter positioning mechanism 400 can add or remove one or more positions and/or filters, whenever it is needed.

In one embodiment, the filter positioning mechanism 400 is mounted on a high-torque stepping motor 460 that rotates the filter positioning mechanism 400 is instructed to by the system. In one embodiment, a high-torque stepping motor allows for speedy exchange of filters or positions. In one embodiment, the estimated switching time is about ~50-100 ms from one position to another.

In one embodiment, an X-ray system 100 accounts for potential scattering affects that may impact negatively to imaging quality. Scattering increases with increase of body size (thickness and weight). However forearm presents smallest and thinnest part of human body and scattering can be estimated through post-data algorithm if necessary.

In relation to FIG. 4F, in various embodiments, the operation procedure of various embodiments of an X-ray system 100 for dual energy bone densitometry includes any one or more of the following steps, in any order:

a) Turn on the power and warm up the machine.
b) Built-In-Test (BIT).
c) Measure the length of patient forearm (for determination of 33% radius BMD).
d) Input the patient's information from either touch-screen or external computer through wire (USB) or wireless (Wi-Fi or Blue-tooth).
e) Position the patient forearm.
f) Run patient exam. In accord with the example embodiment of FIG. 4A-4C, the X-ray tube power is turned on. 0.8 s delay (including filament preheat and rise time of tube voltage). Positioning mechanism stays in a block shuttered position to avoid radiation exposure. The Positioning mechanism switches to a low energy position. 0.2 second delay. Low energy data acquisition by detector is turned on. Exposure time 0.5-0.9 second. SNR can be optimized by adjusting exposure time according to the thickness of patient forearm. Low energy data transferring and recording (low energy image to be transferred and saved in DDR3 SDRAM temporally)—total time ~0.2 seconds. Simultaneously, positioning mechanism switches to high energy position (0.2 seconds).

High energy data acquisition by detector is on. Exposure time can be 0.3-0.5 seconds. SNR can be optimized by adjusting exposure time according to the thickness of patient forearm. High energy data transferring and recording (high energy image to be transferred and saved in DDR3 SDRAM temporally)—total time ~0.2 seconds. Simultaneously, positioning mechanism switches back to the block position (0.2 seconds) and X-ray tube power off (0.2 seconds).

g) Data processing and display.

h) Data stored in flash memory for permanent storage.

i) User Option: transfer data to external computer/storage by wire (USB) or wireless (Wi-Fi or Blue-tooth) if needed.

j) Next exam: system will be locked "power-off" until delay of 120 seconds from previous exam.

In relation to FIGS. 4A-4F, in various embodiments, the operation procedure of various embodiments of an X-ray system 100 for single energy radiography can include any one or more of the following steps, in any order:

a) Turn on the power and warm up the machine.

b) Built-In-Test (BIT).

c) Input the patient's information from either touch-screen or external computer through wire (USB) or wireless (Wi-Fi or Blue-tooth).

d) Position the patient forearm or hand.

e) Run patient exam. The X-ray tube power is turned on. 0.8 second delay (including filament preheat and rise time of tube voltage). Positioning mechanism stays in a block/shuttered position to avoid radiation exposure. Positioning mechanism switches to low energy position or high energy position. 0.2 s delay. Data acquisition by detector is on. Exposure time 0.4-0.9 seconds. SNR can be optimized by adjusting exposure time according to the thickness of patient forearm or hand. Imaging data to be transferred and saved in DDR3 SDRAM temporally)-total time ~0.2 ms. Simultaneously, positioning mechanism switches back to the block position (0.2 s) and X-ray tube power off (0.2 s).

f) Data processing and display.

g) Data stored in flash memory for permanent storage.

h) User option: transfer data to external computer/storage by wire (USB) or wireless (Wi-Fi or Blue-tooth) if needed.

i) Next exam: system will be locked "power-off" until delay from previous exam. Duration of delay depends on the exposure time according to the rule of 1/60 duty cycle.

Some embodiments and the examples described herein are examples and not intended to be limiting in describing the full scope of compositions and methods of these invention. Equivalent changes, modifications and variations of some embodiments, materials, compositions and methods can be made within the scope of the present invention, with substantially similar results.

What is claimed is:

1. A portable, dual-energy radiographic x-ray imaging and bone density measuring system, comprising:
    a power source selected from the group consisting of: an internal battery, an external battery, an internal AC power source, an external AC power source, an internal DC power source, and an external DC power source;
    an X-ray source configured to emit an X-ray beam through a filter positioning mechanism,
    wherein the X-ray beam comprising a first voltage and a second voltage, the first voltage being higher than the second voltage,
    wherein the filter positioning mechanism comprising a high energy filter, a low energy filter, and a shutter configured to block transmission of the X-ray beam;
    an X-ray imaging detector;
    a housing positioning the X-ray source at a distance from the X-ray beam imaging detector,
    wherein the housing is configured for positioning a bone between the X-ray source and the X-ray imaging beam detector;
    a system configured to activate the X-ray source and to control the position of the filter positioning mechanism and imaging data acquisition.

2. The system of claim 1, wherein the X-ray source is active for at most 2 seconds per exposure.

3. The system of claim 1, wherein the high energy filter provides a high energy component above 40-50 kV for transmission through the filter positioning mechanism.

4. The system of claim 1, wherein the high energy filter comprises copper and at least one of the group consisting of tin and rhodium.

5. The system of claim 1, wherein the low energy filter limits transmission of energy below 40-50 kV through the filter positioning mechanism.

6. The system of claim 1, wherein the low energy filter comprises aluminum and at least one type of material having a K-edge absorption at least 40 kV.

7. The system of claim 1, wherein the low energy filter comprises at least one type of material having a K-edge absorption of at least 40 kV is selected from the group consisting of cerium, samarium, gadolinium, and barium.

8. The system of claim 1, wherein the filter positioning mechanism is actuated by a stepper motor in electric communication with the embedded system.

9. The system of claim 8, wherein the filter positioning mechanism is a filter exchanger configured to be rotatably or linearly actuated by the stepper motor.

10. The system of claim 9, wherein the stepper motor is a high torque and high speed design that enables to switch one position to another in 100 ms or less.

11. The system of claim 1, wherein the embedded system provides high-speed/high bandwidth data transmission configured for transmission of imaging data in less than 100 ms.

12. The system of claim 1, wherein the X-ray imaging detector transmits image data through any one of the group consisting of an Ethernet and a camera link.

13. The system of claim 1, wherein the embedded system operates the X-ray source at a duty cycle of approximately 1/60, for a one second active pulsed radiation to sixty second inactive period.

14. The system of claim 1, wherein the embedded chip system operates the X-ray source at a duty cycle for a two second active pulsed radiation to one hundred twenty second inactive period.

15. The system of claim 1, wherein the embedded system comprises an operating system configured to process data, control a LCD/touchscreen, and control a communication from the group consisting of a USB communication and a wireless communication.

16. A method for measuring peripheral bone density, comprising:
    positioning a bone of a patient between an X-ray source and a beam detector in an X-ray system, the X-ray source configured to emit an X-ray beam with a first voltage and a second voltage, wherein the first voltage is higher than the second voltage;
    activating an embedded chip in said X-ray system, the embedded chip configured to activate the X-ray source and to control the voltage, wherein said activating the embedded chip comprises:
        activating the X-ray source for two seconds or less;

moving a filter positioning mechanism from a shuttered position to a first energy position;

acquiring first energy data;

moving the filter positioning mechanism from the first energy position to a second energy position; and acquiring second energy data.

17. A portable, single-energy radiographic x-ray system, comprising:

an X-ray monoblock configured to emit an X-ray beam through a filter positioning mechanism, wherein the X-ray beam comprises a high voltage and a higher voltage, wherein the filter positioning mechanism comprises a high energy filter, a low energy filter, and a shutter configured to block transmission of the X-ray beam;

an X-ray imaging detector;

an anti-scattering grid between the X-ray monoblock and the X-ray imaging detector;

a housing positioning the X-ray source at a distance from the X-ray beam detector, wherein the housing is configured for positioning a portion of a bone between the X-ray source and the X-ray beam detector;

an embedded system configured to activate the X-ray source and to control the position of the filter positioning mechanism and imaging data acquisition.

18. The system of claim 17, configured for a single exposure.

19. The system of claim 18, configured for a continued pulse exposure.

* * * * *